(12) United States Patent (10) Patent No.: US 8,870,916 B2
Ewers et al. (45) Date of Patent: Oct. 28, 2014

(54) LOW PROFILE TISSUE ANCHORS, TISSUE ANCHOR SYSTEMS, AND METHODS FOR THEIR DELIVERY AND USE

(75) Inventors: Richard C. Ewers, Fullerton, CA (US); Tracy D. Maahs, Rancho Santa Margarita, CA (US); Shirley Vong, Aliso Viejo, CA (US)

(73) Assignee: USGI Medical, Inc, San Clemente, CA (US)

( * ) Notice: Subject to any disclaimer, the term of this patent is extended or adjusted under 35 U.S.C. 154(b) by 452 days.

(21) Appl. No.: 11/773,933

(22) Filed: Jul. 5, 2007

(65) Prior Publication Data

US 2008/0009888 A1 Jan. 10, 2008

Related U.S. Application Data

(60) Provisional application No. 60/819,054, filed on Jul. 7, 2006.

(51) Int. Cl.
*A61B 17/04* (2006.01)
*A61B 17/00* (2006.01)
*A61B 17/28* (2006.01)
*A61B 17/29* (2006.01)
*A61B 17/06* (2006.01)
*A61B 17/22* (2006.01)

(52) U.S. Cl.
CPC ..... *A61B 17/0401* (2013.01); *A61B 2017/0496* (2013.01); *A61B 2017/00862* (2013.01); *A61B 2017/00986* (2013.01); *A61B 2017/00004* (2013.01); *A61B 17/282* (2013.01); *A61B 2017/0409* (2013.01); *A61B 17/29* (2013.01); *A61B 2017/0451* (2013.01); *A61B 2017/00526* (2013.01); *A61B 2017/0403* (2013.01); *A61B 17/0487* (2013.01); *A61B 2017/0458* (2013.01); *A61B 2017/061* (2013.01); *A61B 17/22031* (2013.01); *A61B 2017/0417* (2013.01)
USPC .......................................... 606/232

(58) Field of Classification Search
CPC ........... A61B 17/0401; A61B 17/0487; A61B 17/22031; A61B 17/282; A61B 17/29; A61B 2017/0004; A61B 2017/00526; A61B 2017/00862; A61B 2017/00986; A61B 2017/0403; A61B 2017/0409; A61B 2017/0417; A61B 2017/0451; A61B 2017/0458; A61B 2017/049; A61B 2017/061
USPC ........................ 606/151–156, 213–221, 232; 623/23.72–23.74
See application file for complete search history.

(56) References Cited

U.S. PATENT DOCUMENTS 2,201,610 A 5/1940 Dawson
2,413,142 A 12/1946 Jones et al.

(Continued)

FOREIGN PATENT DOCUMENTS

EP 480428 A2 4/1992
EP 847727 A1 6/1998

(Continued)

OTHER PUBLICATIONS

Bluett et al., "Experimental Evaluation of Staple Lines in Gastric Surgery," *Arch. Surg.*, vol. 122, (Jul. 1987), pp. 772-776.

(Continued)

*Primary Examiner* — Julian W Woo
(74) *Attorney, Agent, or Firm* — Kenneth H Ohriner; Perkins Coie LLP

(57) ABSTRACT

Tissue anchors include a flat, broad, and large contact surface for engagement with a portion of tissue. Several embodiments of composite tissue anchors include a support element and an overlay element. Tissue anchor assemblies include two or more tissue anchors, a connector, and a cinching mechanism. In some embodiments, the tissue anchors included in the tissue anchor assemblies are of different types, sizes, and/or shapes.

22 Claims, 17 Drawing Sheets

(56) References Cited

U.S. PATENT DOCUMENTS

| | | |
|---|---|---|
| 3,143,916 A | 8/1964 | Rice |
| 3,150,379 A | 9/1964 | Brown |
| 3,166,072 A | 1/1965 | Sullivan, Jr. |
| 3,316,796 A | 5/1967 | Young |
| 3,494,006 A | 2/1970 | Brumlik |
| 3,551,987 A | 1/1971 | Wilkinson |
| 3,646,615 A | 3/1972 | Ness |
| 3,664,345 A | 5/1972 | Dabbs et al. |
| 3,753,438 A | 8/1973 | Wood et al. |
| 3,867,944 A | 2/1975 | Samuels |
| 3,874,388 A | 4/1975 | King et al. |
| 3,910,281 A | 10/1975 | Kletschka et al. |
| 3,976,079 A | 8/1976 | Samuels et al. |
| 4,006,747 A | 2/1977 | Kronenthal et al. |
| 4,007,743 A | 2/1977 | Blake |
| 4,060,089 A | 11/1977 | Noiles |
| 4,069,825 A | 1/1978 | Akiyama |
| 4,121,487 A | 10/1978 | Bone |
| 4,235,238 A | 11/1980 | Ogiu et al. |
| 4,245,624 A | 1/1981 | Komiya |
| 4,367,746 A | 1/1983 | Derechinsky |
| 4,414,720 A | 11/1983 | Crooms |
| 4,430,998 A | 2/1984 | Harvey et al. |
| 4,462,402 A | 7/1984 | Burgio et al. |
| 4,494,531 A | 1/1985 | Gianturco |
| 4,532,926 A | 8/1985 | O'Holla |
| 4,534,350 A | 8/1985 | Golden et al. |
| 4,548,202 A | 10/1985 | Duncan |
| 4,586,503 A | 5/1986 | Kirsch et al. |
| 4,592,339 A | 6/1986 | Kuzmak et al. |
| 4,592,356 A | 6/1986 | Gutierrez |
| 4,595,007 A | 6/1986 | Mericle |
| 4,610,250 A | 9/1986 | Green |
| 4,669,473 A | 6/1987 | Richards et al. |
| 4,705,040 A | 11/1987 | Mueller et al. |
| 4,711,002 A | 12/1987 | Kreeger |
| 4,724,840 A | 2/1988 | McVay et al. |
| 4,750,492 A | 6/1988 | Jacobs |
| 4,765,335 A | 8/1988 | Schmidt et al. |
| 4,828,439 A | 5/1989 | Giannuzzi |
| 4,832,055 A | 5/1989 | Palestrant |
| 4,841,888 A | 6/1989 | Mills et al. |
| 4,873,976 A | 10/1989 | Schreiber |
| 4,878,270 A | 11/1989 | Westerkamp |
| 4,890,615 A | 1/1990 | Caspari et al. |
| 4,923,461 A | 5/1990 | Caspari et al. |
| 4,929,240 A | 5/1990 | Kirsch et al. |
| 4,957,498 A | 9/1990 | Caspari et al. |
| 5,013,316 A | 5/1991 | Goble et al. |
| 5,032,127 A | 7/1991 | Frazee et al. |
| 5,035,692 A | 7/1991 | Lyon et al. |
| 5,037,433 A | 8/1991 | Wilk et al. |
| 5,041,129 A | 8/1991 | Hayhurst et al. |
| 5,059,201 A | 10/1991 | Asnis |
| 5,073,166 A | 12/1991 | Parks et al. |
| 5,088,979 A | 2/1992 | Filipi et al. |
| 5,100,418 A | 3/1992 | Yoon et al. |
| 5,108,420 A | 4/1992 | Marks |
| 5,122,136 A | 6/1992 | Guglielmi et al. |
| 5,123,914 A | 6/1992 | Cope |
| RE34,021 E | 8/1992 | Mueller et al. |
| 5,176,691 A | 1/1993 | Pierce |
| 5,201,746 A | 4/1993 | Shichman |
| 5,203,864 A | 4/1993 | Phillips |
| 5,217,471 A | 6/1993 | Burkhart |
| 5,217,473 A | 6/1993 | Yoon |
| 5,222,508 A | 6/1993 | Contarini |
| 5,222,961 A | 6/1993 | Nakao et al. |
| 5,222,963 A | 6/1993 | Brinkerhoff et al. |
| 5,224,946 A | 7/1993 | Hayhurst et al. |
| 5,234,430 A | 8/1993 | Huebner |
| 5,234,445 A | 8/1993 | Walker et al. |
| 5,236,445 A | 8/1993 | Hayhurst et al. |
| 5,250,053 A | 10/1993 | Snyder |
| 5,254,126 A | 10/1993 | Filipi et al. |
| 5,258,000 A * | 11/1993 | Gianturco ..................... 606/151 |
| 5,258,015 A | 11/1993 | Li et al. |
| 5,258,016 A | 11/1993 | DiPoto et al. |
| 5,261,916 A | 11/1993 | Engelson |
| 5,268,001 A | 12/1993 | Nicholson et al. |
| 5,269,809 A * | 12/1993 | Hayhurst et al. .............. 606/232 |
| 5,282,827 A | 2/1994 | Kensey et al. |
| 5,284,488 A | 2/1994 | Sideris |
| 5,304,184 A | 4/1994 | Hathaway et al. |
| 5,304,195 A | 4/1994 | Twyford, Jr. et al. |
| 5,304,204 A | 4/1994 | Bregen |
| 5,316,543 A | 5/1994 | Eberbach |
| 5,330,503 A | 7/1994 | Yoon |
| 5,333,624 A * | 8/1994 | Tovey ........................... 128/897 |
| 5,334,217 A | 8/1994 | Das |
| 5,342,376 A | 8/1994 | Ruff |
| 5,345,949 A | 9/1994 | Shlain |
| 5,350,399 A | 9/1994 | Erlebacher et al. |
| 5,354,298 A | 10/1994 | Lee et al. |
| 5,366,459 A | 11/1994 | Yoon |
| 5,366,460 A * | 11/1994 | Eberbach ....................... 606/151 |
| 5,366,478 A * | 11/1994 | Brinkerhoff et al. .......... 606/213 |
| 5,366,479 A | 11/1994 | McGarry et al. |
| 5,370,661 A | 12/1994 | Branch |
| 5,372,146 A | 12/1994 | Branch |
| 5,372,604 A | 12/1994 | Trott |
| 5,374,275 A | 12/1994 | Bradley et al. |
| 5,380,334 A | 1/1995 | Torrie et al. |
| 5,382,231 A | 1/1995 | Shlain |
| 5,395,030 A | 3/1995 | Kuramoto et al. |
| 5,397,331 A * | 3/1995 | Himpens et al. .............. 606/151 |
| 5,403,326 A | 4/1995 | Harrison et al. |
| 5,403,329 A | 4/1995 | Hinchcliffe |
| 5,417,691 A | 5/1995 | Hayhurst |
| 5,417,699 A | 5/1995 | Klein et al. |
| 5,423,856 A | 6/1995 | Green |
| 5,425,744 A | 6/1995 | Fagan et al. |
| 5,429,598 A | 7/1995 | Waxman et al. |
| 5,431,666 A | 7/1995 | Sauer et al. |
| 5,433,721 A | 7/1995 | Hooven et al. |
| 5,433,727 A | 7/1995 | Sideris |
| 5,437,644 A | 8/1995 | Nobles |
| 5,437,680 A | 8/1995 | Yoon |
| 5,437,681 A | 8/1995 | Meade et al. |
| 5,445,167 A | 8/1995 | Yoon et al. |
| 5,451,235 A | 9/1995 | Lock et al. |
| 5,458,609 A | 10/1995 | Gordon et al. |
| 5,462,560 A | 10/1995 | Stevens |
| 5,462,561 A | 10/1995 | Voda |
| 5,465,894 A | 11/1995 | Clark et al. |
| 5,470,337 A | 11/1995 | Moss |
| 5,470,338 A | 11/1995 | Whitfield et al. |
| 5,476,470 A | 12/1995 | Fitzgibbons, Jr. |
| 5,478,354 A | 12/1995 | Tovey et al. |
| 5,480,403 A | 1/1996 | Lee et al. |
| 5,480,405 A | 1/1996 | Yoon |
| 5,496,332 A | 3/1996 | Sierra et al. |
| 5,496,334 A | 3/1996 | Klundt et al. |
| 5,499,991 A | 3/1996 | Garman et al. |
| 5,501,691 A | 3/1996 | Goldrath |
| 5,507,802 A | 4/1996 | Imran |
| 5,507,811 A | 4/1996 | Koike et al. |
| 5,520,691 A | 5/1996 | Branch |
| 5,520,701 A | 5/1996 | Lerch |
| 5,522,843 A | 6/1996 | Zang |
| 5,527,321 A | 6/1996 | Hinchliffe |
| 5,527,322 A | 6/1996 | Klein et al. |
| 5,527,342 A | 6/1996 | Pietrzak et al. |
| 5,531,759 A | 7/1996 | Kensey et al. |
| 5,531,788 A | 7/1996 | Dibie et al. |
| 5,540,704 A | 7/1996 | Gordon et al. |
| 5,549,618 A | 8/1996 | Fleenor et al. |
| 5,549,621 A | 8/1996 | Bessler et al. |
| 5,562,684 A | 10/1996 | Kammerer |
| 5,562,686 A | 10/1996 | Sauer et al. |
| 5,562,688 A | 10/1996 | Riza |
| 5,569,274 A | 10/1996 | Rapacki et al. |
| 5,569,306 A | 10/1996 | Thal |
| 5,571,116 A | 11/1996 | Bolanos et al. |

(56) References Cited

U.S. PATENT DOCUMENTS

| | | |
|---|---|---|
| 5,571,119 A | 11/1996 | Atala |
| 5,573,540 A | 11/1996 | Yoon |
| 5,573,548 A | 11/1996 | Nazre et al. |
| 5,578,045 A | 11/1996 | Das |
| 5,582,616 A | 12/1996 | Bolduc et al. |
| 5,584,835 A | 12/1996 | Greenfield |
| 5,584,859 A | 12/1996 | Brotz |
| 5,601,557 A | 2/1997 | Hayhurst |
| 5,601,558 A | 2/1997 | Torrie et al. |
| 5,603,718 A | 2/1997 | Xu |
| 5,613,974 A | 3/1997 | Andreas et al. |
| 5,613,975 A | 3/1997 | Christy |
| 5,620,461 A * | 4/1997 | Muijs Van De Moer et al. ............... 606/213 |
| 5,626,588 A | 5/1997 | Sauer et al. |
| 5,626,614 A | 5/1997 | Hart |
| 5,630,540 A | 5/1997 | Blewett |
| 5,632,752 A | 5/1997 | Buelna |
| 5,637,097 A | 6/1997 | Yoon |
| 5,643,274 A | 7/1997 | Sander et al. |
| 5,643,289 A | 7/1997 | Sauer et al. |
| 5,643,295 A | 7/1997 | Yoon |
| 5,643,317 A | 7/1997 | Pavcnik et al. |
| 5,643,320 A | 7/1997 | Lower et al. |
| 5,658,312 A | 8/1997 | Green et al. |
| 5,658,313 A | 8/1997 | Thal |
| 5,662,654 A | 9/1997 | Thompson |
| 5,662,662 A | 9/1997 | Bishop et al. |
| 5,662,663 A | 9/1997 | Shallman |
| 5,665,109 A | 9/1997 | Yoon |
| 5,665,112 A | 9/1997 | Thal |
| 5,665,117 A | 9/1997 | Rhodes |
| 5,667,513 A | 9/1997 | Torrie et al. |
| 5,669,917 A | 9/1997 | Sauer et al. |
| 5,679,005 A | 10/1997 | Einstein |
| 5,683,417 A | 11/1997 | Cooper |
| 5,683,419 A | 11/1997 | Thal |
| 5,690,655 A | 11/1997 | Hart et al. |
| 5,693,060 A | 12/1997 | Martin |
| 5,695,525 A * | 12/1997 | Mulhauser et al. ............ 606/151 |
| 5,700,273 A | 12/1997 | Buelna et al. |
| 5,702,397 A | 12/1997 | Goble et al. |
| 5,702,419 A | 12/1997 | Berry et al. |
| 5,702,421 A | 12/1997 | Schneidt |
| 5,707,362 A | 1/1998 | Yoon |
| 5,707,394 A | 1/1998 | Miller et al. |
| 5,709,707 A | 1/1998 | Lock et al. |
| 5,709,708 A | 1/1998 | Thal |
| 5,713,903 A | 2/1998 | Sander et al. |
| 5,718,717 A | 2/1998 | Bonutti |
| 5,720,765 A | 2/1998 | Thal |
| 5,724,978 A | 3/1998 | Tenhoff |
| 5,725,552 A | 3/1998 | Kotula et al. |
| 5,732,707 A | 3/1998 | Widder et al. |
| 5,733,325 A | 3/1998 | Robinson et al. |
| 5,741,297 A | 4/1998 | Simon |
| 5,746,752 A | 5/1998 | Burkhart |
| 5,746,755 A | 5/1998 | Wood et al. |
| 5,749,893 A | 5/1998 | Vidal et al. |
| 5,752,963 A | 5/1998 | Allard et al. |
| 5,766,189 A | 6/1998 | Matsuno |
| 5,769,816 A | 6/1998 | Barbut et al. |
| 5,769,887 A | 6/1998 | Brown et al. |
| 5,776,150 A | 7/1998 | Nolan et al. |
| 5,779,719 A | 7/1998 | Klein et al. |
| 5,782,859 A | 7/1998 | Nicholas et al. |
| 5,782,865 A | 7/1998 | Grotz |
| 5,787,897 A | 8/1998 | Kieturakis |
| 5,792,152 A | 8/1998 | Klein et al. |
| 5,792,153 A | 8/1998 | Swain et al. |
| 5,797,929 A | 8/1998 | Andreas et al. |
| 5,797,960 A | 8/1998 | Stevens et al. |
| 5,800,521 A | 9/1998 | Orth |
| 5,810,849 A | 9/1998 | Kontos |
| 5,810,851 A | 9/1998 | Yoon |
| 5,810,853 A | 9/1998 | Yoon |
| 5,814,064 A | 9/1998 | Daniel et al. |
| 5,814,070 A | 9/1998 | Borzone et al. |
| 5,817,107 A | 10/1998 | Schaller |
| 5,817,110 A | 10/1998 | Kronner |
| 5,823,956 A | 10/1998 | Roth et al. |
| 5,824,011 A | 10/1998 | Stone et al. |
| 5,827,298 A | 10/1998 | Hart et al. |
| 5,829,447 A | 11/1998 | Stevens et al. |
| 5,836,913 A | 11/1998 | Orth et al. |
| 5,836,955 A | 11/1998 | Buelna et al. |
| 5,840,078 A | 11/1998 | Yerys |
| 5,843,084 A | 12/1998 | Hart et al. |
| 5,843,126 A | 12/1998 | Jameel |
| 5,843,167 A | 12/1998 | Dwyer et al. |
| 5,846,261 A | 12/1998 | Kotula et al. |
| 5,855,569 A | 1/1999 | Komi |
| 5,855,614 A | 1/1999 | Stevens et al. |
| 5,860,991 A | 1/1999 | Klein et al. |
| 5,861,003 A * | 1/1999 | Latson et al. ................. 606/213 |
| 5,868,749 A | 2/1999 | Reed |
| 5,868,762 A | 2/1999 | Cragg et al. |
| 5,879,371 A | 3/1999 | Gardiner et al. |
| 5,882,340 A | 3/1999 | Yoon |
| 5,887,594 A | 3/1999 | LoCicero, III |
| 5,888,247 A | 3/1999 | Benetti |
| 5,891,168 A | 4/1999 | Thal |
| 5,891,193 A | 4/1999 | Robinson et al. |
| 5,893,856 A | 4/1999 | Jacob et al. |
| 5,895,404 A | 4/1999 | Ruiz |
| 5,897,562 A | 4/1999 | Bolanos et al. |
| 5,899,920 A | 5/1999 | DeSatnick et al. |
| 5,899,921 A | 5/1999 | Caspari et al. |
| 5,901,895 A | 5/1999 | Heaton et al. |
| 5,902,321 A | 5/1999 | Caspari et al. |
| 5,902,334 A | 5/1999 | Dwyer et al. |
| 5,906,621 A | 5/1999 | Secrest et al. |
| 5,916,224 A | 6/1999 | Esplin |
| 5,916,225 A * | 6/1999 | Kugel ......................... 606/151 |
| 5,925,059 A | 7/1999 | Palermo et al. |
| 5,928,244 A | 7/1999 | Tovey et al. |
| 5,928,264 A | 7/1999 | Sugarbaker et al. |
| 5,935,107 A | 8/1999 | Taylor et al. |
| 5,935,161 A | 8/1999 | Robinson et al. |
| 5,944,738 A * | 8/1999 | Amplatz et al. ............... 606/213 |
| 5,944,739 A | 8/1999 | Zlock et al. |
| 5,947,983 A | 9/1999 | Solar et al. |
| 5,947,997 A | 9/1999 | Pavcnik et al. |
| 5,948,000 A | 9/1999 | Larsen et al. |
| 5,948,001 A | 9/1999 | Larsen |
| 5,954,732 A | 9/1999 | Hart et al. |
| 5,954,766 A | 9/1999 | Zadno-Azizi et al. |
| 5,961,440 A | 10/1999 | Schweich, Jr. et al. |
| 5,961,546 A | 10/1999 | Robinson et al. |
| 5,964,765 A | 10/1999 | Fenton, Jr. et al. |
| 5,964,782 A | 10/1999 | Lafontaine et al. |
| 5,964,783 A | 10/1999 | Grafton et al. |
| 5,968,047 A | 10/1999 | Reed |
| 5,976,127 A | 11/1999 | Lax |
| 5,976,158 A | 11/1999 | Adams et al. |
| 5,976,159 A | 11/1999 | Bolduc et al. |
| 5,976,174 A * | 11/1999 | Ruiz ............................. 606/213 |
| 5,980,558 A | 11/1999 | Wiley |
| 5,984,933 A | 11/1999 | Yoon |
| 5,993,476 A | 11/1999 | Groiso |
| 6,004,347 A | 12/1999 | McNamara et al. |
| 6,013,083 A | 1/2000 | Bennett |
| 6,019,768 A | 2/2000 | Wenstrom, Jr. et al. |
| 6,027,523 A | 2/2000 | Schmieding |
| 6,033,430 A | 3/2000 | Bonutti |
| 6,036,699 A | 3/2000 | Andreas et al. |
| 6,045,497 A | 4/2000 | Schweich, Jr. et al. |
| 6,045,551 A | 4/2000 | Bonutti |
| 6,045,573 A | 4/2000 | Wenstrom, Jr. et al. |
| 6,050,936 A | 4/2000 | Schweich, Jr. et al. |
| 6,053,935 A | 4/2000 | Brenneman et al. |
| 6,056,770 A * | 5/2000 | Epstein et al. ................. 606/213 |
| 6,059,715 A | 5/2000 | Schweich, Jr. et al. |
| 6,059,719 A | 5/2000 | Yamamoto et al. |

(56) References Cited

U.S. PATENT DOCUMENTS

| | | | |
|---|---|---|---|
| 6,068,648 A | 5/2000 | Cole et al. | |
| 6,074,395 A | 6/2000 | Trott et al. | |
| 6,074,401 A | 6/2000 | Gardiner et al. | |
| 6,077,214 A | 6/2000 | Mortier et al. | |
| 6,077,281 A * | 6/2000 | Das | 606/151 |
| 6,077,291 A | 6/2000 | Das | |
| 6,077,297 A | 6/2000 | Robinson et al. | |
| 6,079,414 A | 6/2000 | Roth | |
| 6,086,591 A | 7/2000 | Bojarski | |
| 6,086,600 A | 7/2000 | Kortenbach | |
| 6,099,553 A | 8/2000 | Hart et al. | |
| 6,110,183 A | 8/2000 | Cope | |
| 6,113,609 A | 9/2000 | Adams | |
| 6,113,611 A | 9/2000 | Allen et al. | |
| 6,119,913 A | 9/2000 | Adams et al. | |
| 6,132,438 A | 10/2000 | Fleischman et al. | |
| 6,149,658 A | 11/2000 | Gardiner et al. | |
| 6,152,935 A | 11/2000 | Kammerer et al. | |
| 6,152,946 A | 11/2000 | Broome et al. | |
| 6,159,146 A | 12/2000 | El Gazayerli | |
| 6,159,235 A | 12/2000 | Kim | |
| 6,162,168 A | 12/2000 | Schweich, Jr. et al. | |
| 6,165,119 A | 12/2000 | Schweich, Jr. et al. | |
| 6,165,120 A | 12/2000 | Schweich, Jr. et al. | |
| 6,167,889 B1 | 1/2001 | Benetti | |
| 6,171,320 B1 | 1/2001 | Monassevitch | |
| 6,174,320 B1 * | 1/2001 | Kugel et al. | 606/151 |
| 6,174,323 B1 | 1/2001 | Biggs et al. | |
| 6,176,863 B1 * | 1/2001 | Kugel et al. | 606/151 |
| 6,179,195 B1 | 1/2001 | Adams et al. | |
| 6,183,411 B1 | 2/2001 | Mortier et al. | |
| RE37,117 E | 3/2001 | Palermo | |
| 6,197,022 B1 | 3/2001 | Baker | |
| 6,206,886 B1 | 3/2001 | Bennett | |
| 6,214,007 B1 | 4/2001 | Anderson | |
| 6,214,029 B1 * | 4/2001 | Thill et al. | 606/213 |
| 6,231,561 B1 | 5/2001 | Frazier et al. | |
| 6,238,412 B1 | 5/2001 | Dubrul et al. | |
| 6,241,748 B1 | 6/2001 | Adams | |
| 6,241,768 B1 * | 6/2001 | Agarwal et al. | 623/11.11 |
| 6,245,079 B1 | 6/2001 | Nobles et al. | |
| 6,260,552 B1 | 7/2001 | Mortier et al. | |
| 6,261,222 B1 | 7/2001 | Schweich, Jr. et al. | |
| 6,264,602 B1 | 7/2001 | Mortier et al. | |
| 6,270,515 B1 | 8/2001 | Linden et al. | |
| 6,280,453 B1 * | 8/2001 | Kugel et al. | 606/151 |
| 6,283,973 B1 | 9/2001 | Hubbard et al. | |
| 6,287,315 B1 | 9/2001 | Wijeratne et al. | |
| 6,290,674 B1 | 9/2001 | Roue et al. | |
| 6,290,702 B1 | 9/2001 | Fucci et al. | |
| 6,290,708 B1 * | 9/2001 | Kugel et al. | 606/151 |
| 6,293,956 B1 | 9/2001 | Crainich et al. | |
| 6,296,641 B2 | 10/2001 | Burkhead et al. | |
| 6,296,656 B1 | 10/2001 | Bolduc et al. | |
| 6,299,448 B1 | 10/2001 | Zdrahala et al. | |
| 6,306,159 B1 | 10/2001 | Schwartz et al. | |
| 6,306,163 B1 | 10/2001 | Fitz | |
| 6,312,437 B1 | 11/2001 | Kortenbach | |
| 6,315,789 B1 | 11/2001 | Cragg | |
| 6,322,563 B1 | 11/2001 | Cummings et al. | |
| 6,322,580 B1 | 11/2001 | Kanner | |
| 6,328,727 B1 | 12/2001 | Frazier et al. | |
| 6,332,468 B1 | 12/2001 | Benetti | |
| 6,332,863 B1 | 12/2001 | Schweich, Jr. et al. | |
| 6,332,864 B1 | 12/2001 | Schweich, Jr. et al. | |
| 6,332,893 B1 | 12/2001 | Mortier et al. | |
| 6,336,940 B1 | 1/2002 | Graf et al. | |
| 6,346,074 B1 | 2/2002 | Roth | |
| 6,346,109 B1 | 2/2002 | Fucci et al. | |
| 6,348,064 B1 | 2/2002 | Kanner | |
| 6,350,280 B1 * | 2/2002 | Nash et al. | 623/1.36 |
| 6,355,052 B1 | 3/2002 | Neuss et al. | |
| 6,358,197 B1 | 3/2002 | Silverman et al. | |
| 6,363,938 B2 | 4/2002 | Saadat et al. | |
| 6,368,338 B1 | 4/2002 | Konya et al. | |
| 6,368,339 B1 | 4/2002 | Amplatz | |
| 6,379,366 B1 | 4/2002 | Fleischman et al. | |
| 6,387,104 B1 | 5/2002 | Pugsley, Jr. et al. | |
| 6,391,044 B1 | 5/2002 | Yadav et al. | |
| 6,402,679 B1 | 6/2002 | Mortier et al. | |
| 6,402,680 B2 | 6/2002 | Mortier et al. | |
| 6,406,420 B1 | 6/2002 | McCarthy et al. | |
| H2037 H | 7/2002 | Yates et al. | |
| 6,423,087 B1 | 7/2002 | Sawada | |
| 6,425,911 B1 | 7/2002 | Akerfeldt et al. | |
| 6,447,533 B1 | 9/2002 | Adams | |
| 6,464,712 B1 * | 10/2002 | Epstein et al. | 606/213 |
| 6,475,230 B1 | 11/2002 | Bonutti et al. | |
| 6,491,707 B2 * | 12/2002 | Makower et al. | 606/157 |
| 6,491,714 B1 | 12/2002 | Bennett | |
| 6,494,888 B1 | 12/2002 | Laufer et al. | |
| 6,506,190 B1 | 1/2003 | Walshe | |
| 6,506,196 B1 | 1/2003 | Laufer | |
| 6,508,828 B1 | 1/2003 | Akerfeldt et al. | |
| 6,517,542 B1 | 2/2003 | Papay et al. | |
| 6,527,794 B1 | 3/2003 | McDevitt et al. | |
| 6,533,796 B1 | 3/2003 | Sauer et al. | |
| 6,544,267 B1 | 4/2003 | Cole et al. | |
| 6,551,344 B2 * | 4/2003 | Thill | 606/213 |
| 6,554,845 B1 | 4/2003 | Fleenor et al. | |
| 6,558,400 B2 | 5/2003 | Deem et al. | |
| 6,569,188 B2 | 5/2003 | Grafton et al. | |
| 6,572,629 B2 | 6/2003 | Kalloo et al. | |
| 6,575,976 B2 | 6/2003 | Grafton | |
| 6,575,988 B2 * | 6/2003 | Rousseau | 606/151 |
| 6,589,208 B2 | 7/2003 | Ewers et al. | |
| 6,632,234 B2 * | 10/2003 | Kieturakis et al. | 606/190 |
| 6,632,243 B1 | 10/2003 | Zadno-Azizi et al. | |
| 6,641,557 B1 | 11/2003 | Frazier et al. | |
| 6,641,592 B1 | 11/2003 | Sauer et al. | |
| 6,656,194 B1 | 12/2003 | Gannoe et al. | |
| 6,660,023 B2 | 12/2003 | McDevitt et al. | |
| 6,663,639 B1 | 12/2003 | Laufer et al. | |
| 6,669,713 B2 * | 12/2003 | Adams | 606/213 |
| 6,675,810 B2 | 1/2004 | Krag | |
| 6,692,506 B1 | 2/2004 | Ory et al. | |
| 6,695,764 B2 | 2/2004 | Silverman et al. | |
| 6,698,433 B2 | 3/2004 | Krag | |
| 6,712,830 B2 | 3/2004 | Esplin | |
| 6,712,859 B2 * | 3/2004 | Rousseau et al. | 623/23.64 |
| 6,716,232 B1 | 4/2004 | Vidal et al. | |
| 6,719,763 B2 | 4/2004 | Chung et al. | |
| 6,719,764 B1 | 4/2004 | Gellman et al. | |
| 6,719,765 B2 | 4/2004 | Bonutti | |
| 6,736,828 B1 | 5/2004 | Adams et al. | |
| 6,746,460 B2 | 6/2004 | Gannoe et al. | |
| 6,746,472 B2 | 6/2004 | Frazier et al. | |
| 6,755,843 B2 | 6/2004 | Chung et al. | |
| 6,761,722 B2 | 7/2004 | Cole et al. | |
| 6,773,440 B2 | 8/2004 | Gannoe et al. | |
| 6,773,441 B1 | 8/2004 | Laufer et al. | |
| 6,790,213 B2 * | 9/2004 | Cherok et al. | 606/151 |
| 6,800,082 B2 * | 10/2004 | Rousseau | 606/151 |
| 6,821,285 B2 | 11/2004 | Laufer et al. | |
| 6,830,576 B2 | 12/2004 | Fleischman et al. | |
| 6,835,199 B2 | 12/2004 | McGuckin, Jr. et al. | |
| 6,908,473 B2 | 6/2005 | Skiba et al. | |
| 6,917,834 B2 | 7/2005 | Koblish et al. | |
| 6,918,919 B2 | 7/2005 | Krag | |
| 6,932,834 B2 | 8/2005 | Lizardi et al. | |
| 6,986,781 B2 | 1/2006 | Smith | |
| 6,994,717 B2 | 2/2006 | Kónya et al. | |
| 7,025,756 B2 | 4/2006 | Frazier et al. | |
| 7,033,379 B2 | 4/2006 | Peterson | |
| 7,033,387 B2 | 4/2006 | Zadno-Azizi et al. | |
| 7,037,324 B2 | 5/2006 | Martinek | |
| 7,048,754 B2 | 5/2006 | Martin et al. | |
| 7,056,286 B2 | 6/2006 | Ravenscroft et al. | |
| 7,056,333 B2 | 6/2006 | Walshe | |
| 7,081,126 B2 | 7/2006 | McDevitt et al. | |
| 7,083,648 B2 | 8/2006 | Yu et al. | |
| 7,090,690 B2 | 8/2006 | Foerster et al. | |
| 7,160,312 B2 | 1/2007 | Saadat | |
| 7,288,105 B2 * | 10/2007 | Oman et al. | 606/215 |

(56) References Cited

U.S. PATENT DOCUMENTS

| | | |
|---|---|---|
| 7,678,135 B2 | 3/2010 | Maahs et al. |
| 7,736,379 B2 | 6/2010 | Ewers et al. |
| 8,382,800 B2 | 2/2013 | Maahs et al. |
| 2001/0016675 A1 | 8/2001 | Mortier et al. |
| 2001/0025171 A1 | 9/2001 | Mortier et al. |
| 2001/0037129 A1* | 11/2001 | Thill .................... 606/213 |
| 2001/0039434 A1 | 11/2001 | Frazier et al. |
| 2001/0039436 A1 | 11/2001 | Frazier et al. |
| 2001/0041914 A1 | 11/2001 | Frazier et al. |
| 2001/0049509 A1 | 12/2001 | Sekine et al. |
| 2001/0051807 A1 | 12/2001 | Grafton |
| 2001/0051815 A1 | 12/2001 | Esplin |
| 2001/0051816 A1 | 12/2001 | Enzerink et al. |
| 2001/0056282 A1 | 12/2001 | Sonnenschein et al. |
| 2002/0010490 A1 | 1/2002 | Schaller et al. |
| 2002/0013596 A1 | 1/2002 | Krag |
| 2002/0013608 A1 | 1/2002 | ElAttrache et al. |
| 2002/0019649 A1 | 2/2002 | Sikora et al. |
| 2002/0022851 A1 | 2/2002 | Kalloo et al. |
| 2002/0029080 A1 | 3/2002 | Mortier et al. |
| 2002/0040226 A1 | 4/2002 | Laufer et al. |
| 2002/0049458 A1 | 4/2002 | Singhatat |
| 2002/0055757 A1 | 5/2002 | Torre et al. |
| 2002/0058855 A1 | 5/2002 | Schweich et al. |
| 2002/0065534 A1 | 5/2002 | Hermann et al. |
| 2002/0068849 A1 | 6/2002 | Schweich et al. |
| 2002/0072761 A1 | 6/2002 | Abrams et al. |
| 2002/0077524 A1 | 6/2002 | Schweich et al. |
| 2002/0077696 A1 | 6/2002 | Zadno-Azizi et al. |
| 2002/0078967 A1 | 6/2002 | Sixto et al. |
| 2002/0082621 A1 | 6/2002 | Schurr et al. |
| 2002/0082622 A1 | 6/2002 | Kane |
| 2002/0087208 A1 | 7/2002 | Koblish et al. |
| 2002/0091391 A1 | 7/2002 | Cole et al. |
| 2002/0107530 A1 | 8/2002 | Sauer et al. |
| 2002/0111636 A1 | 8/2002 | Fleischman et al. |
| 2002/0111647 A1 | 8/2002 | Khairkhahan et al. |
| 2002/0116012 A1 | 8/2002 | May et al. |
| 2002/0183768 A1 | 12/2002 | Deem et al. |
| 2002/0183787 A1* | 12/2002 | Wahr et al. .................... 606/213 |
| 2002/0193816 A1 | 12/2002 | Laufer et al. |
| 2003/0009085 A1 | 1/2003 | Arai et al. |
| 2003/0036770 A1 | 2/2003 | Markman |
| 2003/0055442 A1 | 3/2003 | Laufer et al. |
| 2003/0065359 A1 | 4/2003 | Weller et al. |
| 2003/0069593 A1 | 4/2003 | Tremulis et al. |
| 2003/0078604 A1 | 4/2003 | Walshe |
| 2003/0105474 A1 | 6/2003 | Bonutti |
| 2003/0109892 A1 | 6/2003 | Deem et al. |
| 2003/0109900 A1 | 6/2003 | Martinek |
| 2003/0130695 A1 | 7/2003 | McDevitt et al. |
| 2003/0135239 A1 | 7/2003 | Gabriel et al. |
| 2003/0139752 A1 | 7/2003 | Pasricha et al. |
| 2003/0158582 A1 | 8/2003 | Bonutti et al. |
| 2003/0167062 A1 | 9/2003 | Gambale et al. |
| 2003/0171651 A1 | 9/2003 | Page et al. |
| 2003/0171760 A1 | 9/2003 | Gambale |
| 2003/0176890 A1 | 9/2003 | Buckman et al. |
| 2003/0181924 A1 | 9/2003 | Yamamoto et al. |
| 2003/0195530 A1* | 10/2003 | Thill .................... 606/151 |
| 2003/0199972 A1 | 10/2003 | Zadno-Azizi et al. |
| 2003/0204205 A1 | 10/2003 | Sauer et al. |
| 2003/0208209 A1 | 11/2003 | Gambale et al. |
| 2003/0212452 A1 | 11/2003 | Zadno-Azizi et al. |
| 2003/0216613 A1 | 11/2003 | Suzuki et al. |
| 2003/0225312 A1 | 12/2003 | Suzuki et al. |
| 2003/0229296 A1 | 12/2003 | Ishikawa et al. |
| 2003/0229350 A1 | 12/2003 | Kay |
| 2003/0236536 A1 | 12/2003 | Grigoryants et al. |
| 2004/0010271 A1 | 1/2004 | Kortenbach |
| 2004/0030347 A1 | 2/2004 | Gannoe et al. |
| 2004/0049095 A1 | 3/2004 | Goto et al. |
| 2004/0059336 A1 | 3/2004 | Lombardo et al. |
| 2004/0059346 A1 | 3/2004 | Adams et al. |
| 2004/0073219 A1 | 4/2004 | Skiba et al. |
| 2004/0082963 A1 | 4/2004 | Gannoe et al. |
| 2004/0088008 A1 | 5/2004 | Gannoe et al. |
| 2004/0092973 A1* | 5/2004 | Chanduszko et al. ......... 606/151 |
| 2004/0092974 A1 | 5/2004 | Gannoe et al. |
| 2004/0093091 A1 | 5/2004 | Gannoe et al. |
| 2004/0098047 A1 | 5/2004 | Frazier et al. |
| 2004/0106925 A1 | 6/2004 | Culbert |
| 2004/0116949 A1 | 6/2004 | Ewers et al. |
| 2004/0122452 A1 | 6/2004 | Deem et al. |
| 2004/0122453 A1 | 6/2004 | Deem et al. |
| 2004/0122456 A1 | 6/2004 | Saadat et al. |
| 2004/0122463 A1 | 6/2004 | Hibler |
| 2004/0122473 A1 | 6/2004 | Ewers et al. |
| 2004/0122474 A1 | 6/2004 | Gellman et al. |
| 2004/0138525 A1 | 7/2004 | Saadat et al. |
| 2004/0138529 A1 | 7/2004 | Wiltshire et al. |
| 2004/0138682 A1 | 7/2004 | Onuki et al. |
| 2004/0147941 A1 | 7/2004 | Takemoto et al. |
| 2004/0147958 A1 | 7/2004 | Lam et al. |
| 2004/0153008 A1 | 8/2004 | Sharf et al. |
| 2004/0153074 A1 | 8/2004 | Bojarski et al. |
| 2004/0162568 A1 | 8/2004 | Saadat et al. |
| 2004/0167546 A1 | 8/2004 | Saadat et al. |
| 2004/0176784 A1 | 9/2004 | Okada |
| 2004/0186349 A1 | 9/2004 | Ewers et al. |
| 2004/0186350 A1 | 9/2004 | Brenneman et al. |
| 2004/0193117 A1 | 9/2004 | Laufer et al. |
| 2004/0193184 A1 | 9/2004 | Laufer et al. |
| 2004/0193193 A1 | 9/2004 | Laufer et al. |
| 2004/0193194 A1 | 9/2004 | Laufer et al. |
| 2004/0194790 A1 | 10/2004 | Laufer et al. |
| 2004/0210243 A1 | 10/2004 | Gannoe et al. |
| 2004/0215216 A1 | 10/2004 | Gannoe et al. |
| 2004/0220595 A1 | 11/2004 | Frazier et al. |
| 2004/0220610 A1* | 11/2004 | Kreidler et al. ............... 606/200 |
| 2004/0220657 A1 | 11/2004 | Nieminen et al. |
| 2004/0225183 A1 | 11/2004 | Michlitsch et al. |
| 2004/0225305 A1 | 11/2004 | Ewers et al. |
| 2004/0243152 A1 | 12/2004 | Taylor et al. |
| 2004/0249362 A1 | 12/2004 | Levine et al. |
| 2004/0249367 A1 | 12/2004 | Saadat et al. |
| 2004/0249392 A1 | 12/2004 | Mikkaichi et al. |
| 2004/0249395 A1 | 12/2004 | Mikkaichi et al. |
| 2004/0254609 A1 | 12/2004 | Esplin |
| 2004/0260317 A1 | 12/2004 | Bloom et al. |
| 2004/0267306 A1 | 12/2004 | Blaeser et al. |
| 2005/0033320 A1 | 2/2005 | McGuckin et al. |
| 2005/0033366 A1 | 2/2005 | Cole et al. |
| 2005/0033395 A1 | 2/2005 | Seifert et al. |
| 2005/0038370 A1 | 2/2005 | Kuth et al. |
| 2005/0043758 A1 | 2/2005 | Golden et al. |
| 2005/0049617 A1 | 3/2005 | Chatlynne et al. |
| 2005/0065397 A1 | 3/2005 | Saadat et al. |
| 2005/0065401 A1 | 3/2005 | Saadat et al. |
| 2005/0065536 A1 | 3/2005 | Ewers et al. |
| 2005/0065547 A1* | 3/2005 | Marino et al. ................ 606/213 |
| 2005/0070931 A1 | 3/2005 | Li et al. |
| 2005/0075653 A1 | 4/2005 | Saadat et al. |
| 2005/0075654 A1 | 4/2005 | Kelleher |
| 2005/0090862 A1 | 4/2005 | McDevitt et al. |
| 2005/0096666 A1 | 5/2005 | Gordon et al. |
| 2005/0101982 A1 | 5/2005 | Ravenscroft et al. |
| 2005/0107663 A1 | 5/2005 | Saadat et al. |
| 2005/0113640 A1 | 5/2005 | Saadat et al. |
| 2005/0119671 A1 | 6/2005 | Reydel et al. |
| 2005/0131451 A1 | 6/2005 | Kleshinski et al. |
| 2005/0137449 A1 | 6/2005 | Nieminen et al. |
| 2005/0137454 A1 | 6/2005 | Saadat et al. |
| 2005/0137455 A1 | 6/2005 | Ewers et al. |
| 2005/0137456 A1 | 6/2005 | Saadat et al. |
| 2005/0137685 A1 | 6/2005 | Nieminen et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137695 A1 | 6/2005 | Salahieh et al. |
| 2005/0137699 A1 | 6/2005 | Salahieh et al. |
| 2005/0137701 A1 | 6/2005 | Salahieh et al. |

(56) References Cited

U.S. PATENT DOCUMENTS

| | | |
|---|---|---|
| 2005/0137702 A1 | 6/2005 | Haug et al. |
| 2005/0143809 A1 | 6/2005 | Salahieh et al. |
| 2005/0149115 A1 | 7/2005 | Roue et al. |
| 2005/0149122 A1 | 7/2005 | McDevitt et al. |
| 2005/0165378 A1 | 7/2005 | Heinrich et al. |
| 2005/0171563 A1 | 8/2005 | Heinrich et al. |
| 2005/0171564 A1 | 8/2005 | Manzo |
| 2005/0192629 A1 | 9/2005 | Saadat et al. |
| 2005/0203488 A1 | 9/2005 | Michlitsch et al. |
| 2005/0203489 A1 | 9/2005 | Saadat et al. |
| 2005/0203500 A1 | 9/2005 | Saadat et al. |
| 2005/0216040 A1 | 9/2005 | Gertner et al. |
| 2005/0228413 A1 | 10/2005 | Binmoeller et al. |
| 2005/0234294 A1 | 10/2005 | Saadat et al. |
| 2005/0234296 A1 | 10/2005 | Saadat et al. |
| 2005/0245945 A1 | 11/2005 | Ewers et al. |
| 2005/0250980 A1 | 11/2005 | Swanstrom et al. |
| 2005/0250984 A1 | 11/2005 | Lam et al. |
| 2005/0250985 A1 | 11/2005 | Saadat et al. |
| 2005/0250986 A1 | 11/2005 | Rothe et al. |
| 2005/0250987 A1 | 11/2005 | Ewers et al. |
| 2005/0250988 A1 | 11/2005 | Ewers et al. |
| 2005/0250990 A1 | 11/2005 | Le et al. |
| 2005/0251091 A1 | 11/2005 | Saadat et al. |
| 2005/0251157 A1 | 11/2005 | Saadat et al. |
| 2005/0251158 A1 | 11/2005 | Saadat et al. |
| 2005/0251159 A1 | 11/2005 | Ewers et al. |
| 2005/0251160 A1 | 11/2005 | Saadat et al. |
| 2005/0251161 A1 | 11/2005 | Saadat et al. |
| 2005/0251162 A1 | 11/2005 | Rothe et al. |
| 2005/0251165 A1 | 11/2005 | Vaughan et al. |
| 2005/0251166 A1 | 11/2005 | Vaughan et al. |
| 2005/0251176 A1 | 11/2005 | Swanstrom et al. |
| 2005/0251177 A1 | 11/2005 | Saadat et al. |
| 2005/0251189 A1 | 11/2005 | Saadat et al. |
| 2005/0251202 A1 | 11/2005 | Ewers et al. |
| 2005/0251205 A1 | 11/2005 | Ewers et al. |
| 2005/0251206 A1 | 11/2005 | Maahs et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0267523 A1 | 12/2005 | Devellian et al. |
| 2005/0272977 A1 | 12/2005 | Saadat et al. |
| 2005/0273138 A1 | 12/2005 | To et al. |
| 2005/0277945 A1 | 12/2005 | Saadat et al. |
| 2005/0277966 A1 | 12/2005 | Ewers et al. |
| 2005/0277975 A1 | 12/2005 | Saadat et al. |
| 2005/0277981 A1 | 12/2005 | Maahs et al. |
| 2005/0277983 A1 | 12/2005 | Saadat et al. |
| 2005/0283231 A1 | 12/2005 | Haug et al. |
| 2006/0009789 A1 | 1/2006 | Gambale et al. |
| 2006/0015125 A1 | 1/2006 | Swain |
| 2006/0020254 A1 | 1/2006 | Hoffmann |
| 2006/0020274 A1 | 1/2006 | Ewers et al. |
| 2006/0020276 A1 | 1/2006 | Saadat et al. |
| 2006/0036267 A1 | 2/2006 | Saadat et al. |
| 2006/0041244 A1 | 2/2006 | Hohmann et al. |
| 2006/0058582 A1 | 3/2006 | Maahs et al. |
| 2006/0058872 A1 | 3/2006 | Salahieh et al. |
| 2006/0100480 A1 | 5/2006 | Ewers et al. |
| 2006/0100579 A1 | 5/2006 | Maahs et al. |
| 2006/0100628 A1 | 5/2006 | Martinek |
| 2006/0111614 A1 | 5/2006 | Saadat et al. |
| 2006/0116719 A1 | 6/2006 | Martinek |
| 2006/0135970 A1 | 6/2006 | Schaller |
| 2006/0135971 A1 | 6/2006 | Swanstrom et al. |
| 2006/0157067 A1 | 7/2006 | Saadat et al. |
| 2006/0161185 A1 | 7/2006 | Saadat et al. |
| 2006/0173507 A1 | 8/2006 | Mrva et al. |
| 2006/0173524 A1 | 8/2006 | Salahieh et al. |
| 2006/0178560 A1 | 8/2006 | Saadat et al. |
| 2006/0178562 A1 | 8/2006 | Saadat et al. |
| 2006/0183975 A1 | 8/2006 | Saadat et al. |
| 2006/0184161 A1 | 8/2006 | Maahs et al. |
| 2006/0184234 A1 | 8/2006 | Frazier et al. |
| 2006/0189845 A1 | 8/2006 | Maahs et al. |
| 2006/0200062 A1 | 9/2006 | Saadat |
| 2006/0217762 A1 | 9/2006 | Maahs et al. |
| 2006/0237022 A1 | 10/2006 | Chen et al. |
| 2006/0237023 A1 | 10/2006 | Cox et al. |
| 2006/0258909 A1 | 11/2006 | Saadat et al. |
| 2006/0271073 A1 | 11/2006 | Lam et al. |
| 2006/0271074 A1 | 11/2006 | Ewers et al. |
| 2006/0271101 A1 | 11/2006 | Saadat et al. |
| 2006/0287666 A1 | 12/2006 | Saadat et al. |
| 2007/0015965 A1 | 1/2007 | Cox et al. |
| 2007/0027358 A1* | 2/2007 | Gertner et al. ................. 600/37 |
| 2007/0079924 A1 | 4/2007 | Saadat et al. |
| 2007/0123840 A1 | 5/2007 | Cox |
| 2007/0142849 A1 | 6/2007 | Ewers et al. |
| 2007/0175488 A1 | 8/2007 | Cox et al. |
| 2008/0009888 A1 | 1/2008 | Ewers et al. |
| 2008/0086155 A1 | 4/2008 | Rothe et al. |
| 2008/0177304 A1 | 7/2008 | Westra et al. |
| 2008/0200930 A1 | 8/2008 | Saadat et al. |
| 2008/0262294 A1 | 10/2008 | Ewers et al. |
| 2008/0262300 A1 | 10/2008 | Ewers et al. |
| 2008/0262525 A1 | 10/2008 | Chang et al. |
| 2008/0262539 A1 | 10/2008 | Ewers et al. |
| 2009/0018552 A1 | 1/2009 | Lam et al. |
| 2009/0023985 A1 | 1/2009 | Ewers |

FOREIGN PATENT DOCUMENTS

| | | |
|---|---|---|
| EP | 1031321 A1 | 8/2000 |
| EP | 1648279 A2 | 4/2006 |
| EP | 1699366 A2 | 9/2006 |
| EP | 1781184 A2 | 5/2007 |
| EP | 1804680 A2 | 7/2007 |
| EP | 1804683 A2 | 7/2007 |
| FR | 2768324 A1 | 3/1999 |
| GB | 2165559 A | 4/1986 |
| JP | 2007513717 | 5/2007 |
| WO | WO 92/04870 | 4/1992 |
| WO | WO 95/19140 | 7/1995 |
| WO | WO 95/25468 | 9/1995 |
| WO | WO 99/22649 | 5/1999 |
| WO | WO 00/40159 | 7/2000 |
| WO | WO 00/57796 | 10/2000 |
| WO | WO 00/78227 | 12/2000 |
| WO | WO 00/78229 | 12/2000 |
| WO | WO 01/21246 | 3/2001 |
| WO | WO 01/66001 | 9/2001 |
| WO | WO 01/66018 | 9/2001 |
| WO | WO 01/85034 | 11/2001 |
| WO | WO 01/87144 | 11/2001 |
| WO | WO 01/89370 | 11/2001 |
| WO | WO 01/89392 | 11/2001 |
| WO | WO 01/89393 | 11/2001 |
| WO | WO 02/00119 | 1/2002 |
| WO | WO 02/24080 | 3/2002 |
| WO | WO 02/39880 | 5/2002 |
| WO | WO 02/060328 | 8/2002 |
| WO | WO 02/064012 | 8/2002 |
| WO | WO 02/085252 | 10/2002 |
| WO | WO 02/094105 | 11/2002 |
| WO | WO 03/007796 | 1/2003 |
| WO | WO 03/007799 | 1/2003 |
| WO | WO 03/090633 | 11/2003 |
| WO | WO 03/092509 | 11/2003 |
| WO | WO 03/094785 | 11/2003 |
| WO | WO 03/096909 | 11/2003 |
| WO | WO 03/099137 | 12/2003 |
| WO | WO 03/105732 | 12/2003 |
| WO | WO 2004/004542 | 1/2004 |
| WO | WO 2004/004544 | 1/2004 |
| WO | WO 2004/019787 | 3/2004 |
| WO | WO 2004/019788 | 3/2004 |
| WO | WO 2004/021865 | 3/2004 |
| WO | WO 2004/021867 | 3/2004 |
| WO | WO 2004/021868 | 3/2004 |
| WO | WO 2004/021873 | 3/2004 |
| WO | WO 2004/021894 | 3/2004 |

(56) References Cited

FOREIGN PATENT DOCUMENTS

| | | |
|---|---|---|
| WO | WO 2004/041119 | 5/2004 |
| WO | WO 2004/056273 | 7/2004 |
| WO | WO 2004/064600 | 8/2004 |
| WO | WO 2004/075787 | 9/2004 |
| WO | WO 2004/084808 | 10/2004 |
| WO | WO 2004/103189 | 12/2004 |
| WO | WO 2004/103430 | 12/2004 |
| WO | WO 2004/110285 | 12/2004 |
| WO | WO 2005/004727 | 1/2005 |
| WO | WO 2005/011463 | 2/2005 |
| WO | WO 2005/011519 | 2/2005 |
| WO | WO 2005/037072 | 4/2005 |
| WO | WO 2005/037152 | 4/2005 |
| WO | WO 2005/048815 | 6/2005 |
| WO | WO 2005/050971 | 6/2005 |
| WO | WO 2005/058239 | 6/2005 |
| WO | WO 2005/086945 | 9/2005 |
| WO | WO 2005/104927 | 11/2005 |
| WO | WO 2005/110244 | 11/2005 |
| WO | WO 2005/122914 | 12/2005 |
| WO | WO 2005/122915 | 12/2005 |
| WO | WO 2006/019868 | 2/2006 |
| WO | WO 2006/039199 | 4/2006 |
| WO | WO 2006/039223 | 4/2006 |
| WO | WO 2006/039296 | 4/2006 |
| WO | WO 2006/078429 | 7/2006 |
| WO | WO 2006/089217 | 8/2006 |
| WO | WO 2006/093975 | 9/2006 |
| WO | WO 2006/110275 | 10/2006 |
| WO | WO 2006/127306 | 11/2006 |
| WO | WO 2007/009021 | 1/2007 |

OTHER PUBLICATIONS

Brolin et at., Experimental Evaluation of Techniques of Gastric Paritioning for Morbid Obesity, *Surgery, Gynecology & Obstetrics*, vol. 153, (Dec. 1981), pp. 878-882.

Okudaira et al., "The Healing and Tensile Strength of the Gastroplasty Staple Line," *The American Surgeon*, Oct. 1984, pp. 564-568.

Surgical Dynamics Inc., The S•D•sorb Meniscal Stapler [brochure] (1997), 2 pages total.

\* cited by examiner

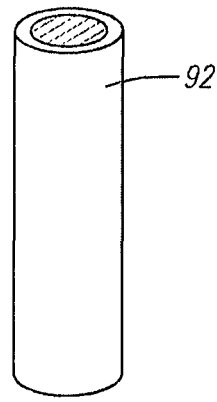
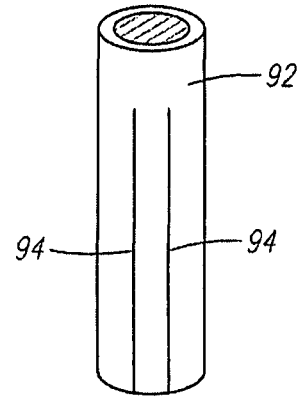
FIG. 3A　　　　　　　　FIG. 3B
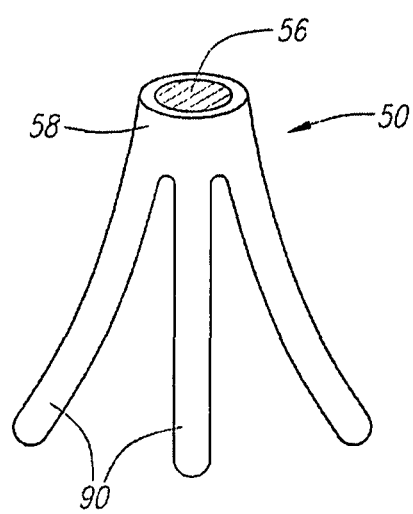
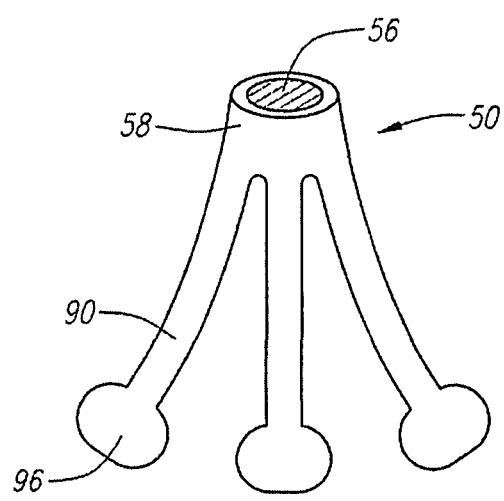
FIG. 3C　　　　　　　　FIG. 3D

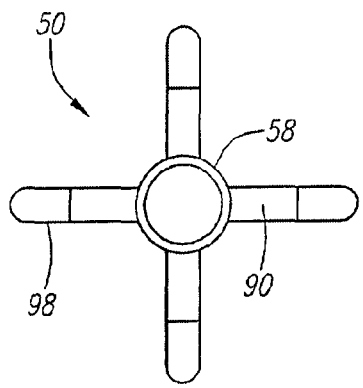
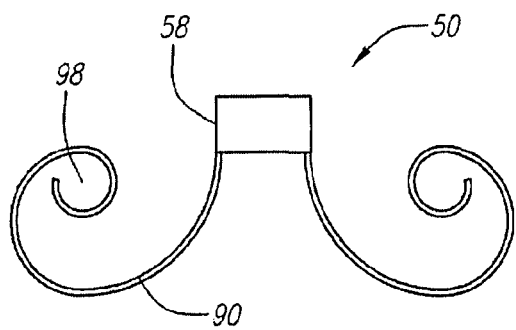
FIG. 4A  FIG. 4B
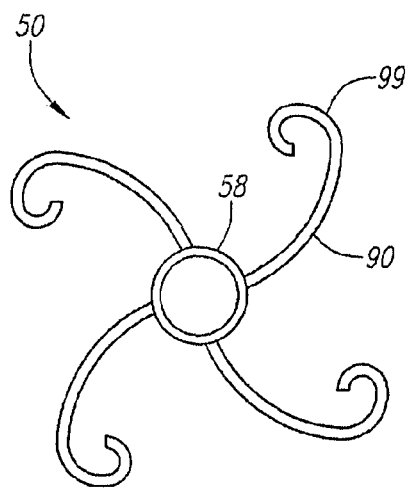
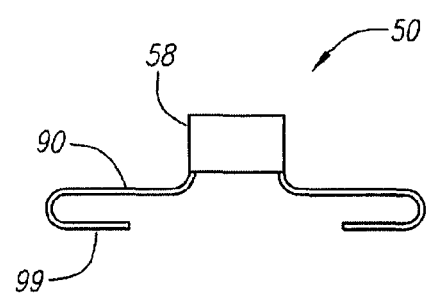
FIG. 5A  FIG. 5B

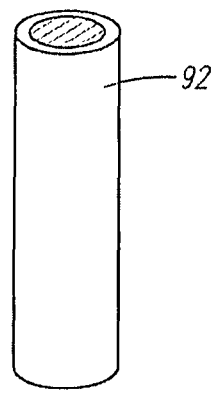
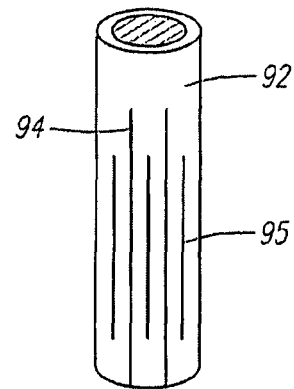
FIG. 6A    FIG. 6B
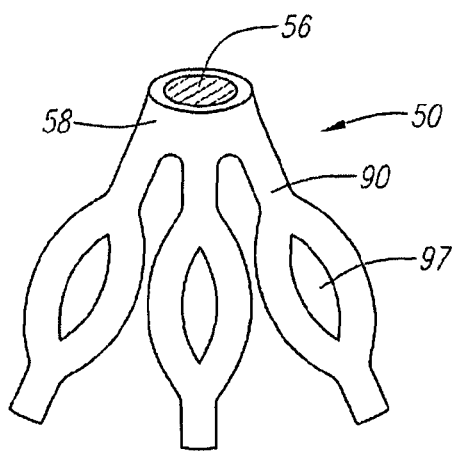
FIG. 6C
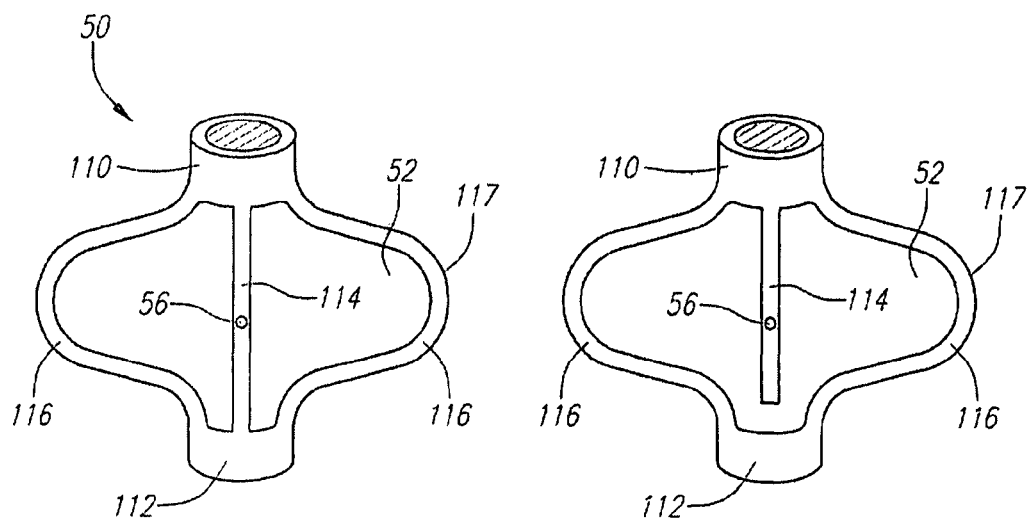
FIG. 7A    FIG. 7B

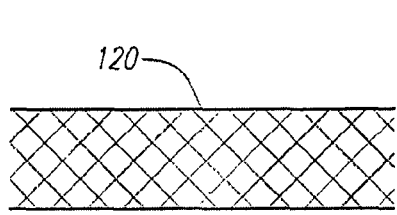
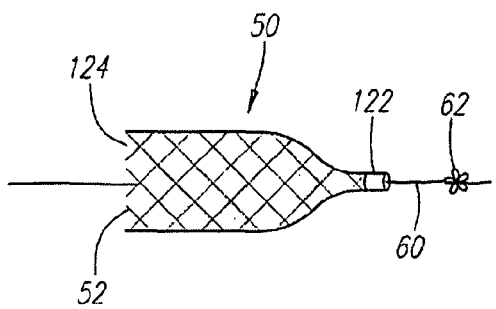
FIG. 8A      FIG. 8B
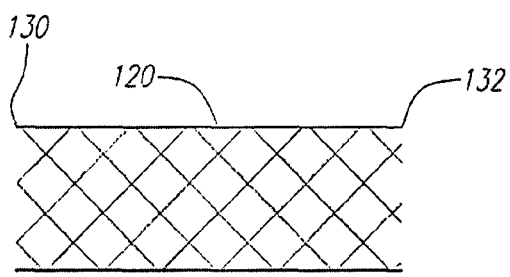
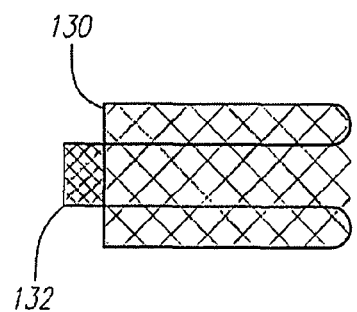
FIG. 9A      FIG. 9B
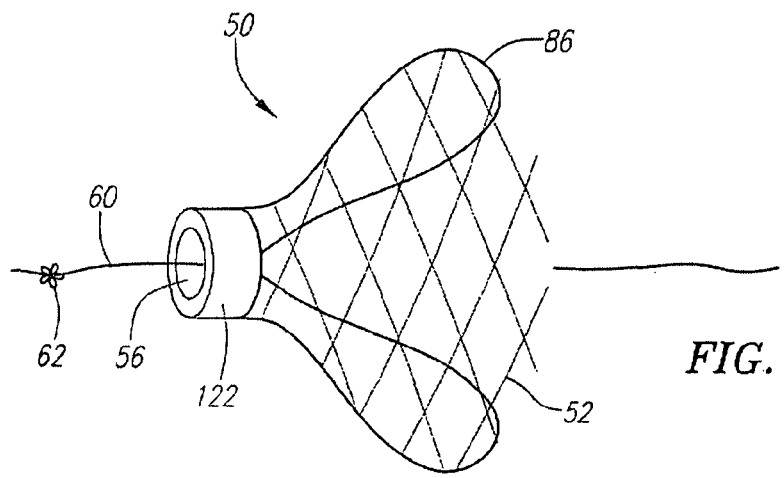
FIG. 9C

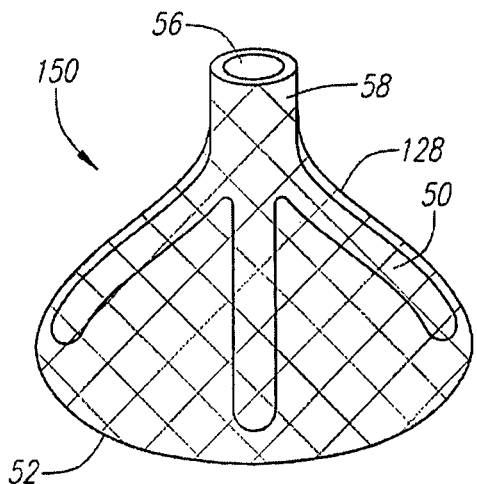
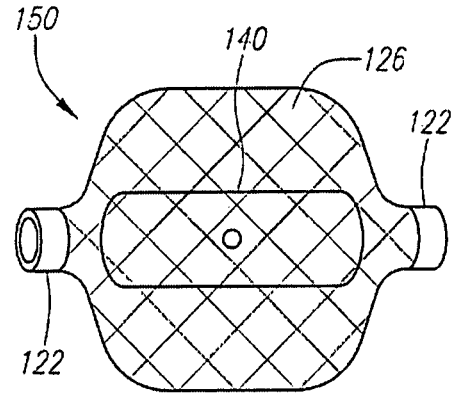
FIG. 13    FIG. 14
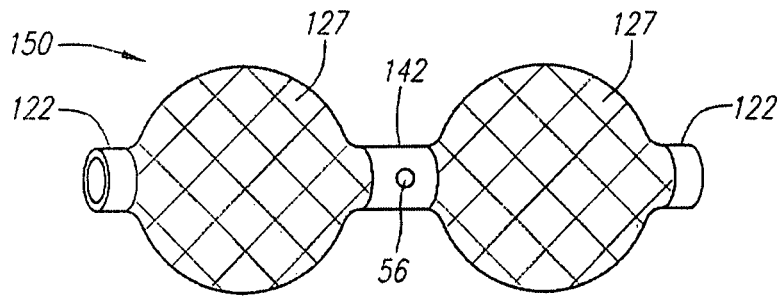
FIG. 15A
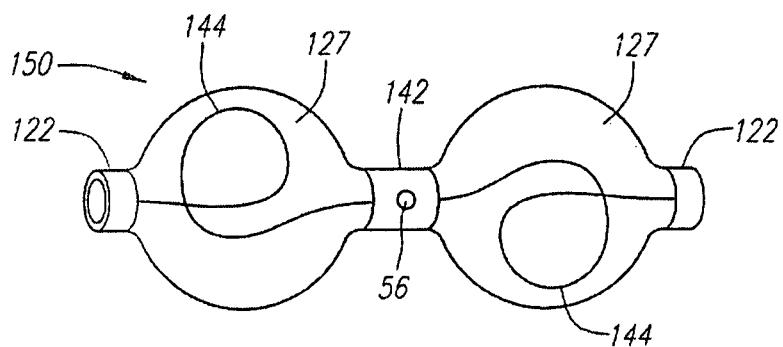
FIG. 15B

LOW PROFILE TISSUE ANCHORS, TISSUE ANCHOR SYSTEMS, AND METHODS FOR THEIR DELIVERY AND USE

RELATED APPLICATION DATA

This application claims priority to U.S. Provisional Patent Application Ser. No. 60/819,054, filed Jul. 7, 2006, entitled "Low Profile Tissue Anchors" which is incorporated herein by reference in its entirety.

FIELD OF THE INVENTION

The present invention relates to methods and apparatus for deploying tissue anchors into or against one or more tissue regions and to tissue anchors that are deployable from a low-profile configuration to an expanded configuration.

BACKGROUND OF THE INVENTION

Many surgical and other therapeutic or diagnostic procedures include steps of reconfiguring, fixing, or otherwise manipulating tissue in some manner, or joining two or more portions of tissue together. Several devices have been used to perform these functions, including sutures, staples, screws, anchors, clips, tags, and other similar types of devices.

Many of the conventional sutures, staples, clips, tags, and anchors that are used in these procedures require extensive training by the clinician to achieve competent use. In addition, many of the devices concentrate significant force over a small surface area of the tissue, thereby potentially causing the suture, staple, or anchor to tear through the tissue.

Many of the procedures require regions of tissue within the body to be approximated towards one another and reliably secured. For example, several surgical procedures are performed in which tissue in the gastrointestinal lumen is approximated, such as gastric reduction. The gastrointestinal lumen includes four tissue layers, wherein the mucosa layer is the inner-most tissue layer followed by connective tissue, the muscularis layer and the serosa layer. One problem with conventional gastric reduction systems is that the anchors (or staples) should engage at least the muscularis tissue layer in order to provide a proper foundation. In other words, the mucosa and connective tissue layers typically are not strong enough to sustain the tensile loads imposed by normal movement of the stomach wall during ingestion and processing of food. In particular, these layers tend to stretch elastically rather than firmly hold the anchors (or staples) in position, and accordingly, the more rigid muscularis and/or serosa layer should ideally be engaged. This problem of capturing the muscularis or serosa layers becomes particularly acute where it is desired to place an anchor or other apparatus transesophageally rather than intraoperatively, since care must be taken in piercing the tough stomach wall not to inadvertently puncture adjacent tissue or organs, One conventional method for securing anchors within a body lumen to the tissue is to utilize sewing devices to suture the stomach wall into folds This procedure typically involves advancing a sewing instrument through the working channel of an endoscope and into the stomach and against the stomach wall tissue. The contacted tissue is then typically drawn into the sewing instrument where one or more sutures or tags are implanted to hold the suctioned tissue in a folded condition known as a plication. Another method involves manually creating sutures for securing the plication.

One of the problems associated with these types of procedures is the time and number of intubations needed to perform the various procedures endoscopically. Another problem is the time required to complete a plication from the surrounding tissue with the body lumen. In the period of time that a patient is anesthetized, procedures such as for the treatment of morbid obesity, GERD, or other procedures must be perfomed to completion. Accordingly, the placement and securement of the tissue plication should ideally be relatively quick and performed with a high level of confidence.

Another problem with conventional securement methods is ensuring that the staple, knotted suture, tag, anchor, or clip is secured tightly against the tissue and that the newly created plication will not relax under any slack which may be created by slipping staples, knots, or clips. Other conventional tissue securement devices such as suture anchors, twist ties, crimps, etc. are also often used to prevent sutures from slipping through tissue. However, many of these types of devices are typically large and unsuitable for low-profile delivery through the body, e.g., transesophageally; transrectally, or transvaginally.

Moreover, when grasping or clamping onto or upon the layers of tissue with conventional anchors, sutures, staples, clips, etc., may of these devices are configured to be placed only after the tissue has been plicated and not during the actual plication procedure.

SUMMARY

In a first aspect, a tissue anchor includes a flat, broad contact surface on a first side and an exposed surface on an opposite side. The flat, broad contact surface allows the tissue anchor to rest substantially flat against the surface of the tissue so that the force imparted by the anchor is substantially evenly distributed over the engagement surface. This feature is believed to facilitate and promote tissue healing and reconfiguration. Tis feature is also believed to increase the holding strength of the tissue anchor system, and increased the resistance to pull-through of the anchor (i.e., the tendency of an anchor to be pulled through a hole or other defect in the tissue under the tension force from the connector). Moreover, the absence of a collar or other component projecting from the contact surface of several of the tissue anchor embodiments described below allows the tissue anchor assemblies incorporating those anchors to more closely approximate portions of tissue, or to approximate portions of thin tissue more effectively than would otherwise be possible with conventional tissue anchor systems.

In several embodiments, the tissue anchor includes a woven material that makes up all or a portion of the contact surface. In some embodiments, the woven material is a mesh or braid formed of a biocompatible and/or bioabsorbable material. In some embodiments, the entire tissue anchor is formed of the woven material. In other embodiments, the tissue anchor includes an overlay of a woven material, such as a woven pouch, that is supported by an underlying support structure, such as a support bar, a support ring, and/or a strutted anchor structure. In still other embodiments, a sheet or plurality of sheets of woven material are supported by a frame formed of a resilient material.

In another aspect a tissue anchor assembly includes at least one distal anchor, at least one proximal anchor, a connector extending between and interconnecting the distal and proximal anchors, and a retainer mechanism that retains the distal and proximal anchors at a substantially maximum distance from each other on the connector when the tissue anchor assembly is deployed through tissue. In some embodiments, the distal anchor and proximal anchor of the tissue anchor assembly are of the same or similar construction. In other embodiments, the distal anchor and proximal anchor are of different constructions. For example, in an embodiment, the distal anchor is a basket-type anchor having a first collar, a second collar, and a collapsible basket structure interposed between the two collars, while the proximal anchor is a flat, composite tissue anchor having a woven pouch containing a support bar and a support ring. In another embodiment, both the proximal and distal anchors are of the composite tissue anchor type described above. These embodiments are exemplary, and are not intended to be limiting. All other combinations that include one or more of the tissue anchors described herein are also contemplated.

In another aspect a delivery device for reconfiguring tissue and delivering a tissue anchor assembly includes a tissue manipulation assembly and a needle deployment assembly. The tissue manipulation assembly includes a flexible shaft and a tissue manipulation end effector adapted to grasp and manipulate tissue. The needle deployment assembly includes a flexible shaft having a hollow needle at its distal end. The needle deployment assembly is adapted to extend through the tissue manipulation assembly shaft, with the hollow needle extending through a portion of tissue held by the tissue manipulation end effector. A tissue anchor or tissue anchor assembly is releasably received in the hollow needle, and is deployed out of the needle deployment assembly under control of the user.

BRIEF DESCRIPTIONS OF THE DRAWINGS

FIGS. 1A-C are side views of three embodiments of tissue anchors.

FIGS. 2A-B are side views of a tissue anchor assembly in a transition state and a deployed state, respectively.

FIGS. 3A-D are side views of a tube and of embodiments of a tissue anchor, illustrating a method of making the tissue anchors.

FIGS. 4A-B are a top view and a side view, respectively, of a tissue anchor.

FIGS. 5A-B are a top view and a side view, respectively, of a tissue anchor.

FIGS. 6A-C are side views of a tube and of an embodiment of a tissue anchor, illustrating a method of making the tissue anchors.

FIGS. 7A-B are side views of two embodiments of a tissue anchor.

FIGS. 8A-B are side views of a mesh sleeve and an open-ended mesh tissue anchor formed from the mesh sleeve, respectively.

FIGS. 9A-C are side views of a mesh sleeve, an inverted mesh sleeve, and a mesh tissue anchor having a non-fraying transition formed from the mesh sleeve, respectively.

FIGS. 10A-B are side views of a mesh sleeve and a mesh pouch formed from the mesh sleeve, respectively.

FIG. 13 is a side view of a composite tissue anchor including a strutted anchor and a mesh anchor overlaying the strutted anchor.

FIG. 14 is a side view of a composite tissue anchor including a T-bar retained within a mesh pouch.

FIGS. 15A-B are side views of a composite tissue anchor including a center collar and a pair of support coils on a mesh pouch.

Figure 16:
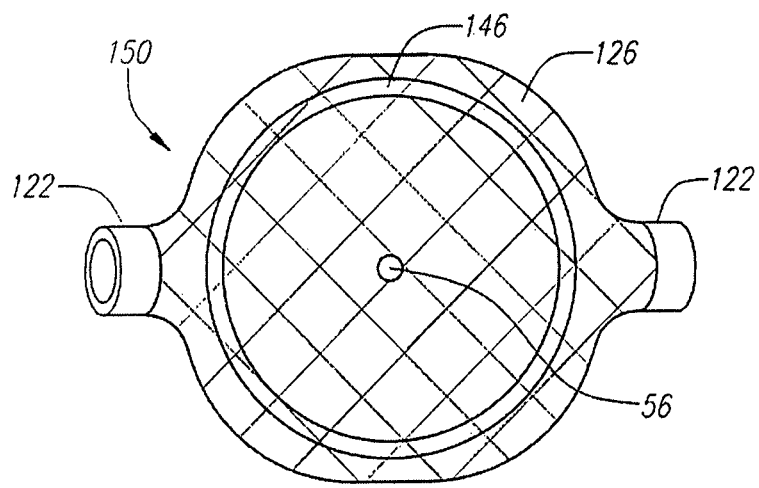

FIG. 16 is a side view of a composite tissue anchor including a support ring retained within a mesh pouch.

Figure 17:
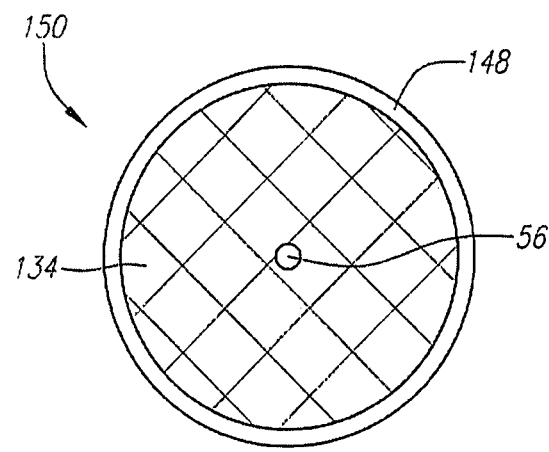

FIG. 17 is a side view of a composite tissue anchor including a mesh sheet attached to a frame.

Figure 18A:
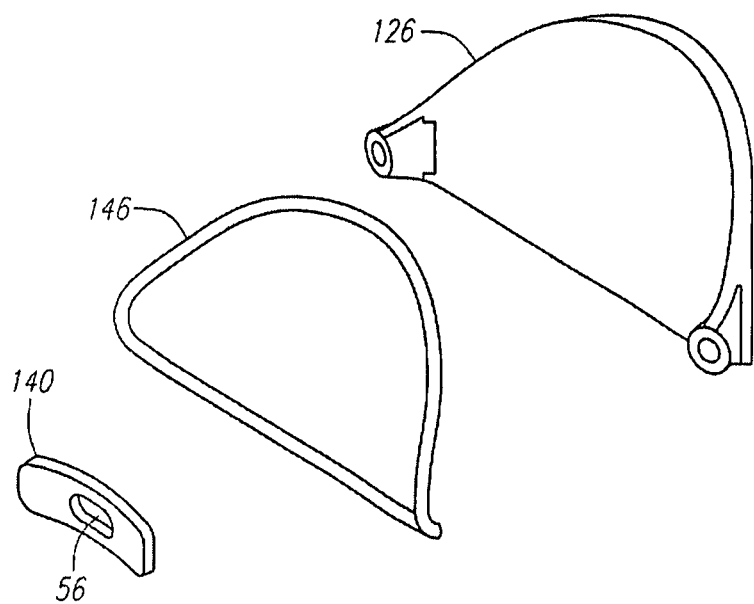
Figure 18B:
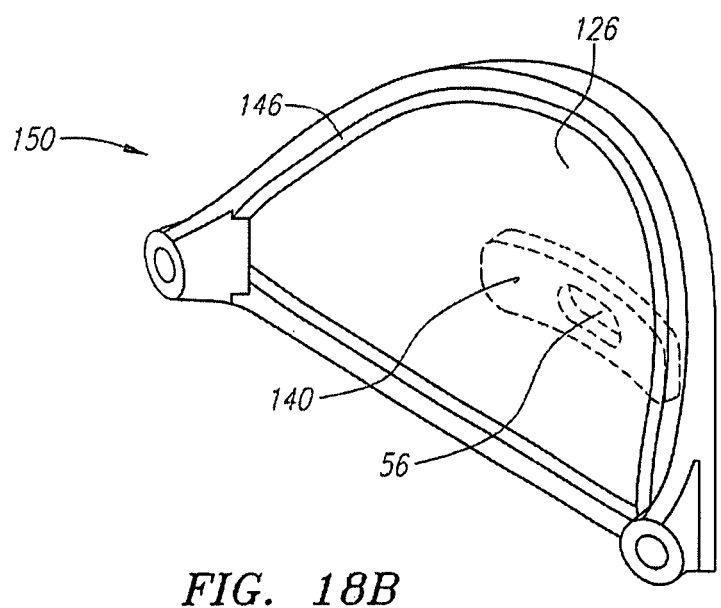

FIGS. 18A-B are and exploded view and a perspective view of a composite tissue anchor including a support ring and a cross-bar retained within a mesh pouch.

Figure 19A:
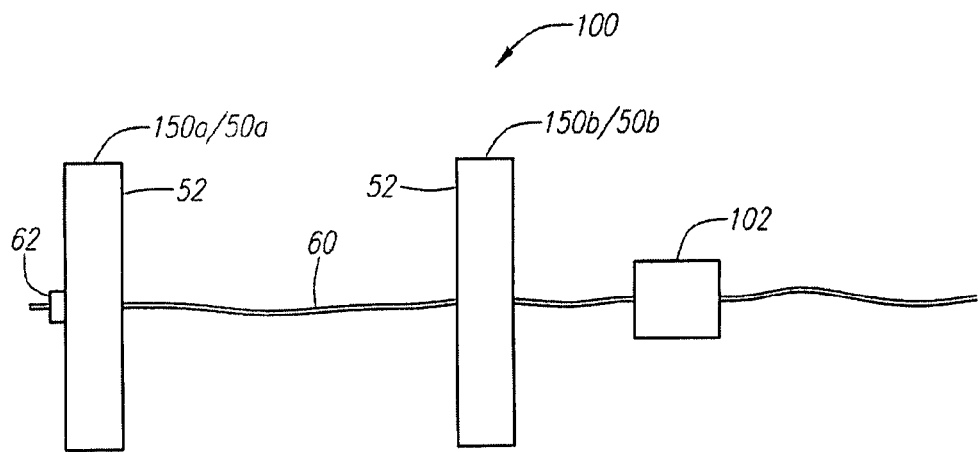
Figure 19B:
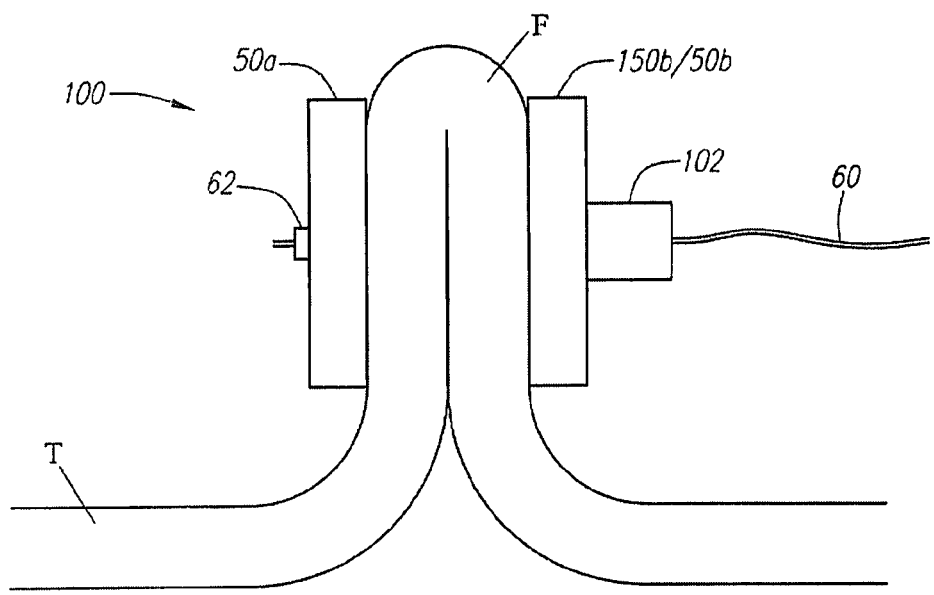

FIGS. 19A-B are side schematic views illustrating a method for approximating a tissue fold using a tissue anchor assembly.

Figure 20A:
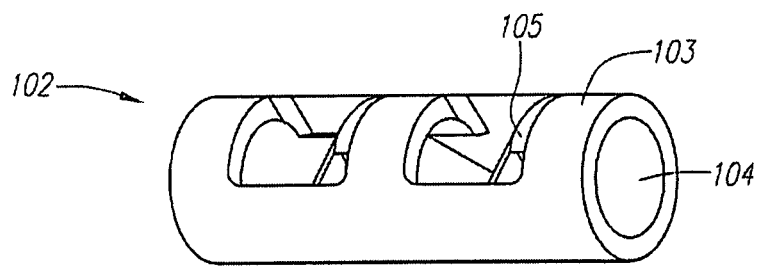
Figure 20B:
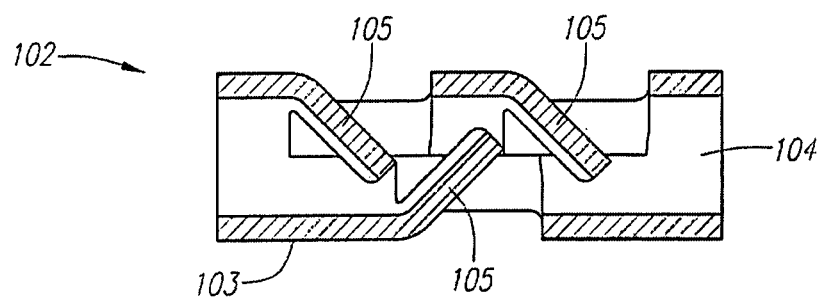

FIGS. 20A-B are perspective and cross-sectional views, respectively, of a cinch.

Figure 21:
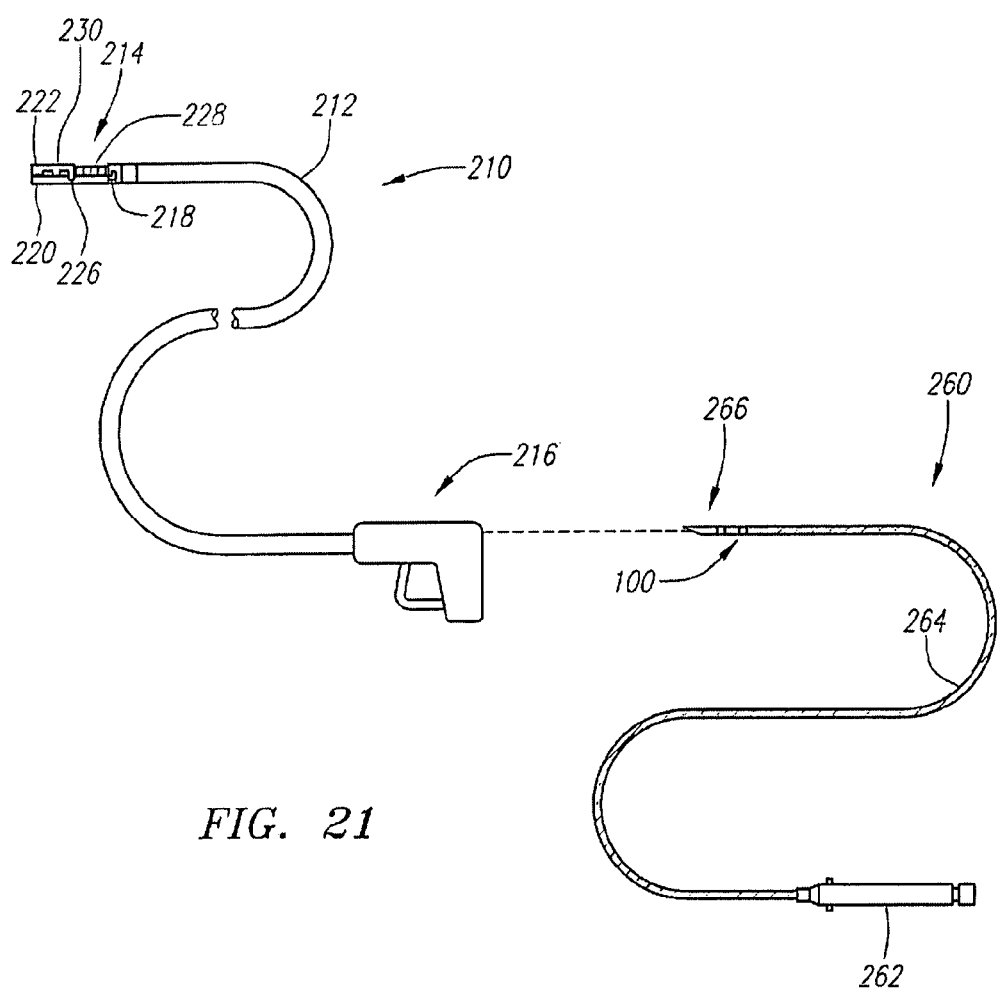

FIG. 21 is an assembly view showing how a needle deployment assembly is introduced through a handle and tubular body of a tissue manipulation assembly.

Figure 22:
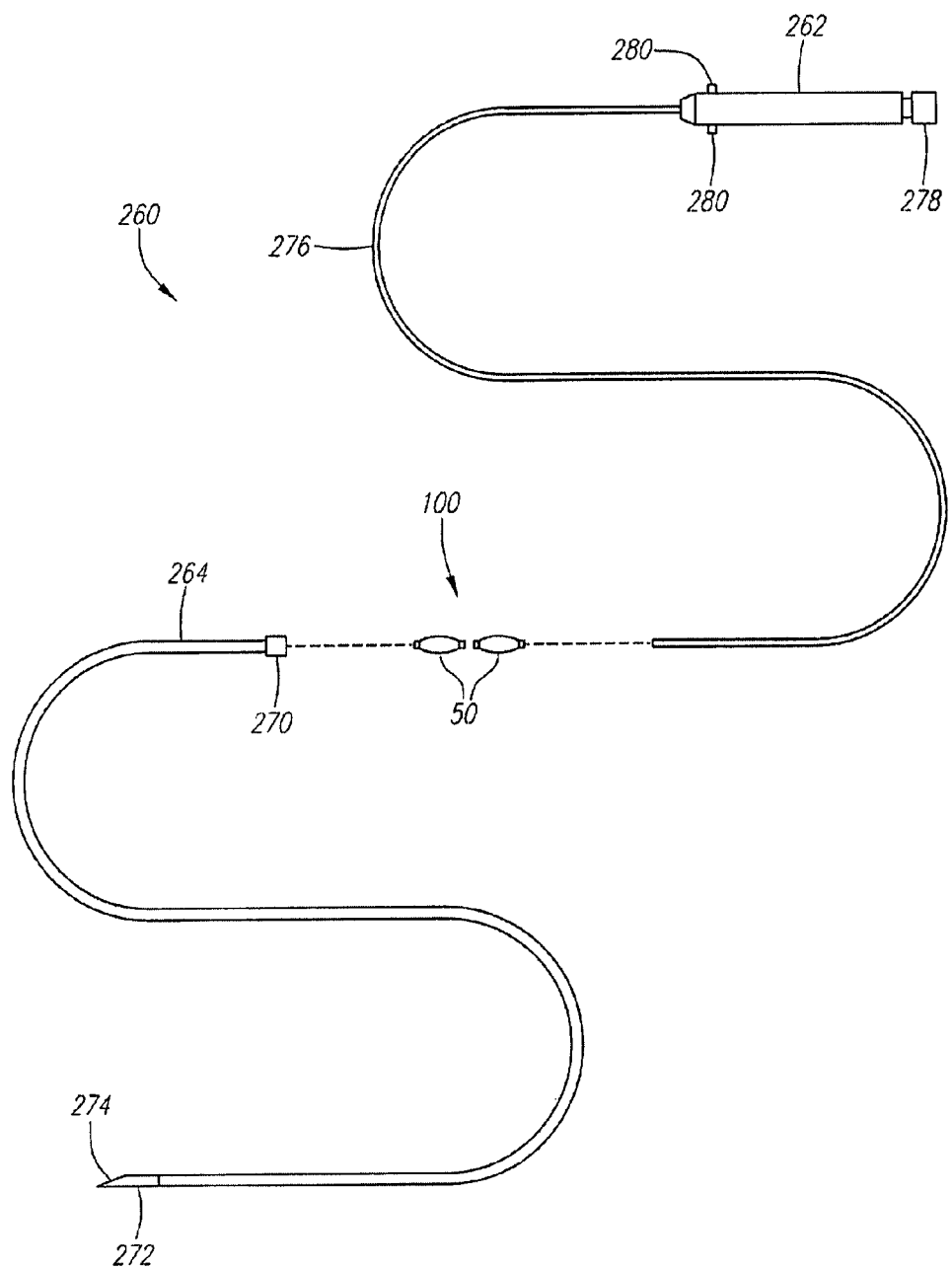

FIG. 22 is an exploded assembly view of the needle deployment assembly from FIG. 21.

Figure 23A:
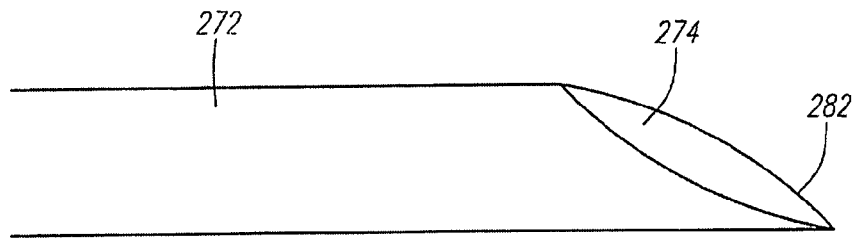
Figure 23B:
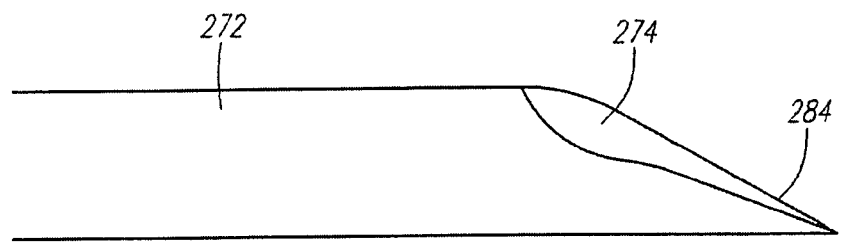
Figure 23C:
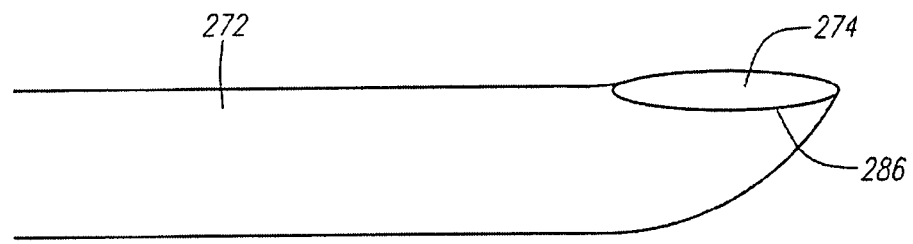

FIGS. 23A-C are side views of three embodiments of a needle body portion of a needle deployment assembly.

Figure 24A:
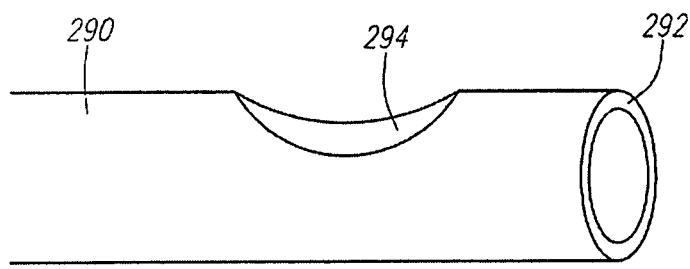

FIG. 24A is a side view of a tube having a side exit port.

Figure 24B:
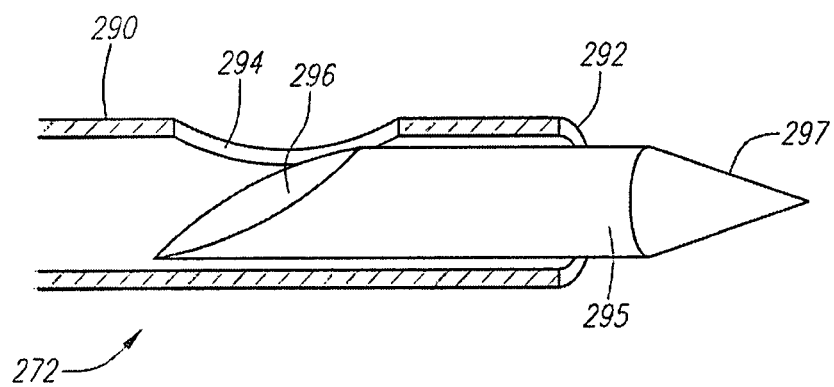

FIG. 24B is a side view of a needle body constructed using the tube of FIG. 248.

Figure 25A:
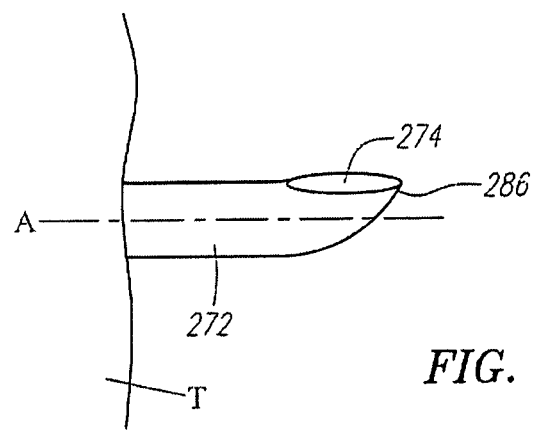
Figure 25B:
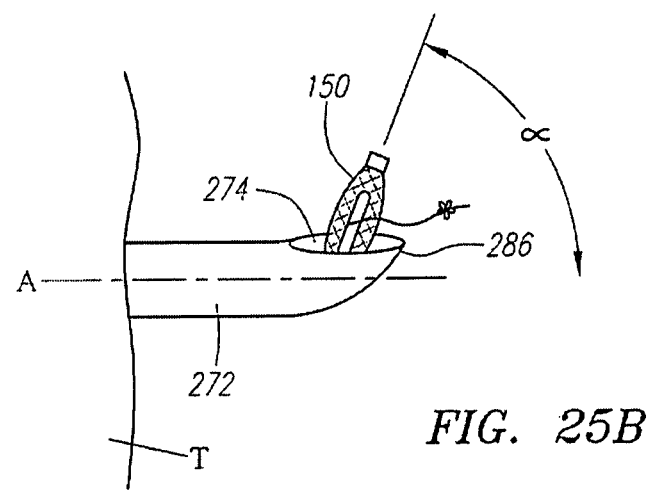
Figure 25C:
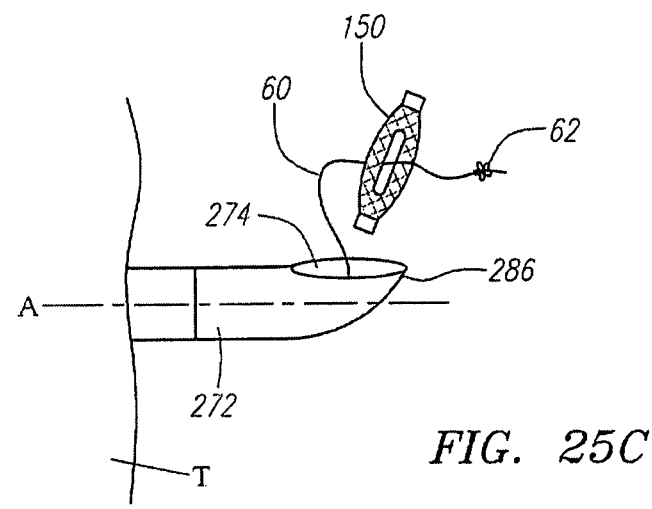

FIGS. 25A-C illustrate deployment of a tissue anchor from a needle body having an end configuration with a deflected point.

DETAILED DESCRIPTION

The devices described herein include several embodiments of tissue anchors, tissue anchor assemblies, and tissue anchor delivery systems. The methods described herein include several embodiments of methods for reconfiguring tissue, methods for joining portions of tissue together, and methods for deploying and using tissue anchors and tissue anchor systems.

The tissue anchors described herein are devices that have a contact surface adapted to engage an engagement surface of a portion of tissue and to coact with a connector, such as a suture, to maintain the tissue in a desired configuration or reconfiguration. In several of the embodiments described herein, the tissue anchors include a flat, large, or broad contact surface. In several of the embodiments, the tissue anchors have a first, low-profile shape and/or size to facilitate delivery, and a second, enlarged shape and/or size for deployment against a portion of tissue to be maintained in a desired configuration or reconfiguration. The tissue anchors are preferably formed of biocompatible and/or bioabsorbable materials.

The tissue anchor assemblies described herein include at least two tissue anchors that are attached to each other either directly or indirectly by a connector, such as a suture. The tissue anchor assemblies also include one or more retainer mechanisms, such as cinches, that perform the functions of retaining and/or adjusting the relative positions of the tissue anchors on the connector.

Several embodiments of tissue anchors and tissue anchor systems are described below in reference to the attached drawings. As noted above, one feature included in several of the tissue anchor embodiments described below is the provision of a substantially flat, large, or broad contact surface for engagement with the tissue when compared with conventional "T"-anchors, collared anchors, "T"-tags, staples, and other similar devices, or when compared with knots used during suturing procedures. The relatively flat, large, or broad contact surface is believed to provide several advantages over the conventional anchors and over conventional suturing procedures. For example, the large contact surface allows the anchor to rest substantially flat against the surface of the tissue so that the force imparted by the anchor is substantially evenly distributed over the engagement surface. This feature is believed to facilitate and promote tissue healing and reconfiguration. This feature is also believed to increase the holding strength of the tissue anchor system, and increased the resistance to pull-through of the anchor (i.e., the tendency of an anchor to be pulled through a hole or other defect in the tissue under the tension force from the connector). Moreover, the absence of a collar or other component projecting from the contact surface of several of the tissue anchor embodiments described below allows the tissue anchor systems incorporating those anchors to more closely approximate portions of tissue, or to approximate portions of thin tissue more effectively than would otherwise be possible with conventional systems.

Figure 1A:
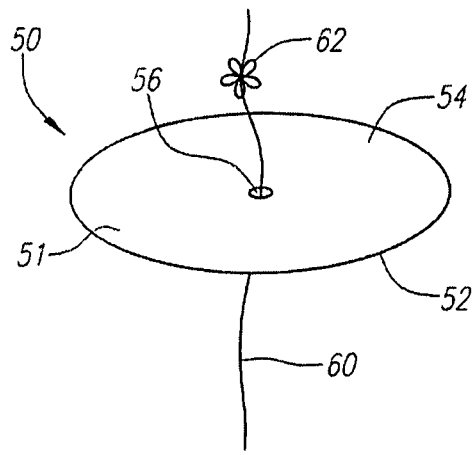
Figure 1B:
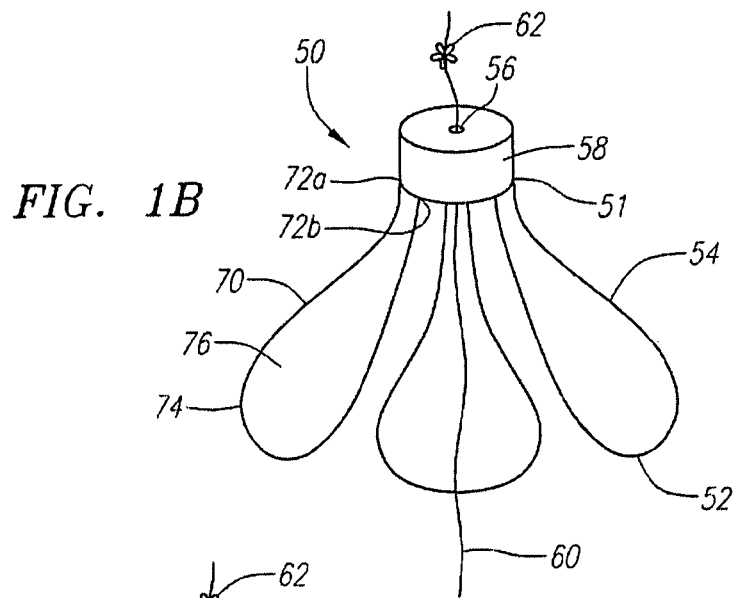
Figure 1C:
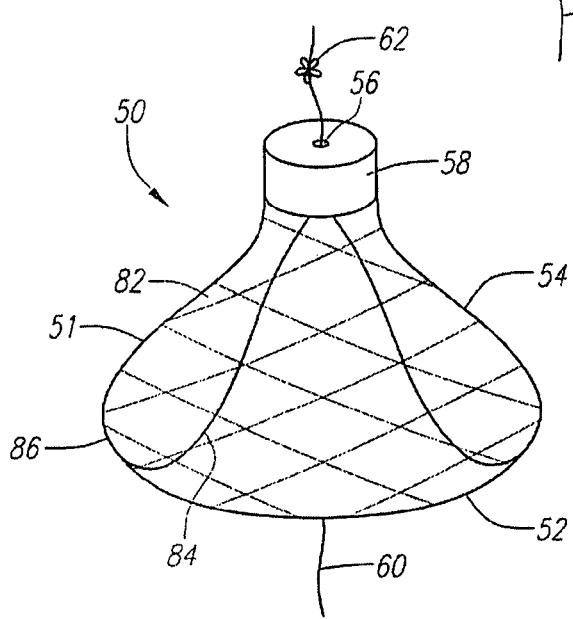

Turning first to FIGS. 1A-C, there are shown several embodiments of tissue anchors 50 suitable for use in the tissue anchor assemblies described herein. In each of the embodiments, the tissue anchor 50 includes a main body 51 having a broad contact surface 52 and an opposite, exposed surface 54. A passage 56 is provided to allow a connector, such as a suture 60, to pass through the anchor 50. A stop member, such as a knot 62 or a block, a bead or other member, is provided on the suture 60. The relative sizes of the knot 62 and the passage 56 are such that the knot 62 is unable to pass through the passage 56, thereby creating the ability for the suture 60 to apply a force to the tissue anchor 50 as the suture 60 is placed under tension.

Although a suture 60 is included in the embodiments illustrated in FIGS. 1A-C as well as several of the embodiments described below, alternative embodiments include connectors having other constructions and connectors formed of other materials. For example, in some embodiments, the connector is a wire, a fiber, a filament, a rod, or other member suitable for performing the functions of the connector.

In the embodiments shown and those described below, the main body 51 portion, the connector, the cinching mechanism, and the other components of the tissue anchor assembly are preferably formed of biocompatible and/or bioabsorbable materials, including but not limited to metals or metallic materials such as stainless steel, titanium, nickel, nickel-titanium alloy (i.e., Nitinol) or other alloys, plastics or other polymeric materials, biocompatible or bioabsorbable (e.g., PGA, PLA, PLG and other lactide-glycolide polymers and copolymers) suture, braid, or mesh, and other medical grade materials conventionally used for tissue anchors, sutures, implants, and similar devices. Several tissue anchor assembly embodiments are formed of combinations of these materials.

The main body 51 and the other components of the tissue anchor 50 are adapted to transition from a low-profile delivery configuration to be releasably received in a delivery device (such as a needle), and then to transition to a deployment configuration after delivery. In some embodiments, the transition to the deployment configuration is caused by spontaneous expansion due to the materials or construction of the tissue anchor 50. In other embodiments, the transition to the deployment configuration is caused or facilitated by retraction of the tissue anchor 50 against tissue.

In the embodiment shown in FIG. 1A, the main body 51 of the tissue anchor is a generally disk-shaped member. Although a circular disk is shown in the illustrated embodiment, other flat shapes (e.g., triangular, rectangular, irregular, etc.) are contemplated in alternative embodiments. The main body 51 is formed of a flexible material adapted to be rolled up or otherwise compressed into a low-profile delivery configuration to be releasably received in a delivery device (such as a needle), and then to transition to a deployment configuration (as shown in FIG. 1A) after delivery. In the deployment configuration, the contact surface 52 of the tissue anchor is able to be placed against the engagement surface of the tissue. As a tension force is applied to the suture 60, the knot 62 engages the exposed surface 54 of the main body 51, biasing it against the tissue.

In the embodiment shown in FIG. 1B, the main body 51 includes a plurality of loops 70 that are each attached to and that radiate from a central collar 58. At least two loops 70 are included, and the upper number of loops is limited only by the size of the loops in relation to the overall tissue anchor. The collar 58 is formed of a relatively rigid biocompatible or bioabsorbable material such as those described above. Each of the loops 70 is a wire of a resilient metal, plastic, or other material. Each loop 70 has two terminal ends 72a, 72b and an enlarged loop end 74 opposite the two terminal ends 72a, 72b. Each of the two terminal ends 72a, 72b is attached near to the other at the collar 58. The loop end 74 extends away from the collar 58 and defines a void space 76 within the loop. Due to its shape and materials, each loop 70 is fairly compressible, such that the loops 70 are able to be compressed into a delivery configuration and then expanded to a deployment, configuration.

In the embodiment shown in FIG. 1C, the main body 51 is a generally cone-shaped member formed of a mesh or braid material. As described more fully below in relation to FIGS. 9A-C, the main body includes in a continuous mesh layer having an upper surface 82 and a lower surface 84, corresponding to the exposed surface 54 and the contact surface 52 of the anchor, respectively. The edges of the mesh layer are joined to the collar 58. In an alternative embodiment the collar 58 is formed by heat fusing the edges of the mesh layer. The transition line 86 defined between the upper surface 82 and lower surface 84 defines the border of the main body 51. Due to its shape and the nature of the mesh material, the main body 51 is fairly compressible such that it is able to be compressed into a delivery configuration and then expanded to a deployment configuration.

Figure 2A:
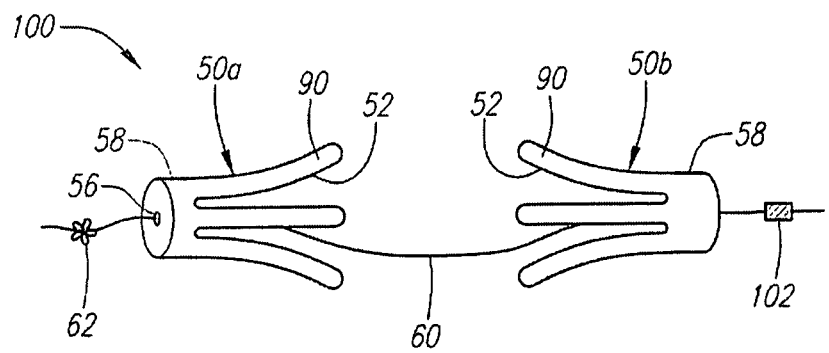
Figure 2B:
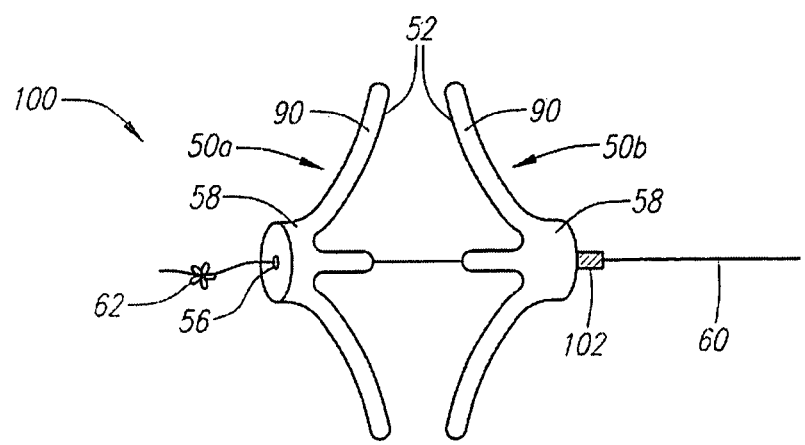

A tissue anchor assembly 100 is shown in FIGS. 2A-B. The tissue anchor assembly 100 includes a pair of tissue anchors including a distal anchor 50a and a proximal anchor 50b, each slidably attached to a connector (e.g., a suture 60), A cinching mechanism, such as a cinch 102, is provided on the suture 60. Additional information concerning the cinching mechanism is described below in relation to FIGS. 20A-B. In the embodiment shown, the anchors 50 each include a plurality of resilient struts 90 extending from and formed integrally with a central collar 58. In an alternative embodiment, the struts 90 are attached to but not integrally formed with the collar 58. The materials and construction of the anchors 50 are described more fully below in relation to FIGS. 3A-C.

FIG. 2A shows the tissue anchor assembly as it would appear in a transition state between delivery and complete deployment. Each of the anchors 50 is slidably attached to the suture 60 at a distance from one another, and the struts 90 are oriented generally in line with the longitudinal axis of the anchor 50. In FIG. 2B, the anchors 50 have been moved into close proximity to one another, and the struts 90 have been biased radially outward, away from the longitudinal axes of the anchors 50. The cinch 102 has been advanced to apply a force biasing the proximal anchor 50b toward the distal anchor 50a. This orientation is consistent with fill deployment of the tissue anchor assembly, such as when a fold of tissue or one or more portions of tissue are interposed between the anchors 50. For clarity, no tissue is shown in FIGS. 2A-B.

The radial extension of the struts 90 of the anchors 50 creates an enlarged contact surface 52 for each of the anchors 50, As described above, the enlarged contact surface 52 provides advantages in applied forces, force distribution, and promotion of healing. In particular, because there is no collar 58 or other similar structure that forms or that is included on the contact surface 52 of the anchors, the contact surfaces 52 of the anchors 50 are able to come into close proximity to one another to more effectively approximate tissue interposed between the anchors.

In FIGS. 3A-D, there is shown a method for manufacturing the tissue anchor 50 described above in relation to FIGS. 2A-B. In FIG. 3A, a tube 92 of Nitinol (nickel-titanium alloy) or other suitable material is provided. The height and inner and outer diameters of the tube 92 are selected to provide desired dimensions of the tissue anchor 50 to be constructed. A plurality of longitudinal slits 94 are cut (e.g., by laser or other suitable cutting device) on the tube. (See FIG. 3B). The slits 94 extend from the bottom end of the tube 92 but do not extend over the entire length, ending at a position that will constitute the bottom end of the collar 58 of the completed anchor 50. After the slits 94 have been cut, the struts 90 formed thereby are flared radially outward, as shown in FIG. 3C. If the anchor material is Nitinol or other shape memory material, the anchor may be heat-set such that the struts 90 flare radially outward upon activation. Otherwise, the elastic properties of the material may be used to create the flared orientation for the struts 90.

In some embodiments, cut-in features are formed on portions of one or more of the struts 90. For example, in FIG. 3D, atraumatic end features 96 are formed on the bottom ends of each of the struts 90. The atraumatic end features 96 are broad, flattened portions at the terminal ends of the struts 90. The broad surfaces reduce the possibility of injury to the tissue. In some embodiments, a protective coating or covering is added to the atraumatic end feature to further enhance the level of protection provided.

FIGS. 4A-B and 5A-B show additional features that are optionally applied to the tissue anchors 50 described above. FIGS. 4A-B and 5A-B show top views and side views, respectively, of tissue anchors 50 formed generally in the manner described above in relation to FIGS. 3A-C. In the embodiment shown in FIGS. 4A-B, the struts 90 are each curled within a vertical plane to form a vertically curled terminal end 98. In the embodiment shown in FIGS. 5A-B, the struts 90 are each curled within a generally horizontal plane to form a horizontally curled terminal end 99. The vertically curled and horizontally curled terminal end features provide variations to the size of the contact surface 52 and to the resiliency of the struts 90 incorporated into the tissue anchors.

FIGS. 6A-C illustrate another embodiment of a method for forming a tissue anchor. Similar to the method described above, a tube of Nitinol or other suitable material is cut to form longitudinal slits 94 which define a plurality of struts 90. In addition, a second plurality of shorter slits 95 is formed between the longitudinal slits 94. The shorter slits do not extend to the bottom end of the tube 92. Instead, the shorter slits 95 are shorter than the lengths of the longitudinal slits 94. After the individual struts 90 are flared radially outward, the shorter slits 95 are expanded to define a void space or pocket 97 in each of the struts 90. The shorter slits may be expanded using, for example, a rod or other structure that is extended through the shorter slit 95 to pry the two sides apart. For those embodiments using Nitinol (or other shape memory material), after the struts 90 are flared radially and the pockets 97 are formed in each of the struts 90, the anchor 50 is heat set in its deployment configuration. The presence of the pockets 97 in each of the struts 90 creates a relatively larger engagement surface or "footprint" for each of the struts to contact the surface of the tissue.

FIGS. 7A-B each show an embodiment of a modified "basket" type anchor formed in a manner similar to the embodiments described above in relation to FIGS. 3A-C and 6A-C. A conventional "basket" anchor has a structure that includes a pair of collars that move toward one another to cause a collapsible "basket" portion extending between the two collars to expand radially. As the two collars move away from one another, the basket portion collapses radially inward. In contrast, the modified anchors described herein have a flat orientation in which the connector extends through the center of the anchor. Turning first to FIG. 7A, the anchor 50 includes an upper collar 110, a lower collar 112, a center strut 114, and a pair of side struts 116. A passage 56, through which a connector (e.g., a suture 60) is allowed to pass, is formed generally near the center of the center strut 114. In the embodiment shown, the components are formed from a tube of material (e.g., Nitinol). In other embodiments, the components are formed from a sheet of material. The side struts 116 each include an elbow portion 117 that extends radially away from the center strut 114. In the embodiment shown, each of the center strut 114 and the two side struts 116 are generally located in a single plane. The resultant anchor 50 thereby defines a generally flat, broad contact surface 52 for engagement with a portion of tissue.

In the embodiment shown in FIG. 7B, the center strut 114 is attached to the upper collar 110 but is not directly attached to the lower collar 112. Accordingly, the center strut 114 forms a cantilever in relation to the upper collar 110.

As noted above, several embodiments of tissue anchors described herein are formed of or incorporate woven materials, such as braid anchor mesh materials. As used herein, the term "mesh" refers to any of a varied, of medical grade flexible woven fabric materials used in surgical and other medical applications. Conventional mesh materials are formed of polymeric (e.g., polyester, nylon, etc.) or metallic (e.g., stainless steel) materials. In several embodiments, the mesh is formed of bioabsorbable materials (e.g., PGA, PLA, PLG, or other lactide-glycolide polymers or copolymers).

Turning next to FIGS. 8A-B, a mesh sleeve 120 has a generally tubular shape. In some embodiments, the structure of the braids making up the mesh creates a disposition for the mesh sleeve to naturally collapse or draw down radially inward toward the longitudinal axis of the sleeve 120. This effect facilitates collapse of an anchor formed of mesh into a low-profile delivery configuration, followed by expansion of the mesh into a deployment configuration.

In addition, as shown in FIG. 8B, in some embodiments, the mesh material is capable of being fused by heating or other treatment. In the embodiment shown, a fused end 122 is formed at one end of the sleeve. The opposite end 124 remains open, thereby defining a contact surface 52 of the anchor 50. The flexibility of the mesh material allows the open end 124 to expand radially, providing a broad, flat contact surface when the anchor 50 is incorporated into a tissue anchor assembly 100.

Turning next to FIGS. 9A-C, a mesh sleeve 120 includes a first end 130 and a second end 132. The sleeve is inverted, and the second end 132 is fed back through the sleeve until it is located radially inward of the first end 130. (See FIG. 9B).

The first end 130 and second end 132 are then heat fused to form a fused end 122 defining a passage 56 therethrough, thereby forming a tissue anchor 50. Relative to the embodiment described above in relation to FIGS. 8A-B, the tissue anchor 50 embodiment includes a transition line 86 that is non-fraying because it is formed of a continuous layer of mesh that has been doubled over.

Figure 10A:
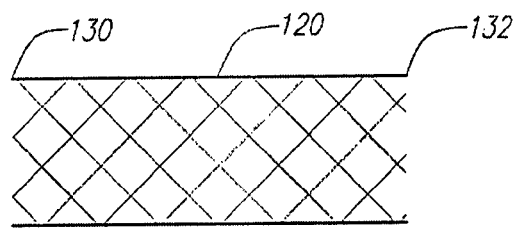
Figure 10B:
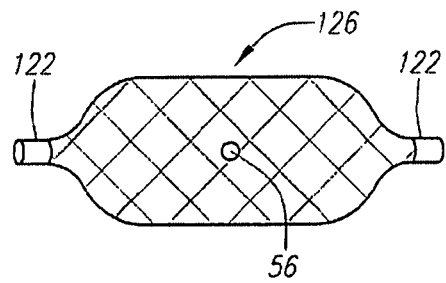

In FIGS. 10A-B, a mesh sleeve 120 is heat fused at both ends 130, 132 to form a mesh pouch 126 having a fused end 122 at both ends. A passage 56 is formed at or near the centroid of the mesh pouch 126. In the embodiment shown, the passage 56 is formed by heat fusing of the layers of mesh material. In other embodiments, an eyelet, a washer, or other similar object is placed within the pouch to define the passage 56.

Figure 11A:
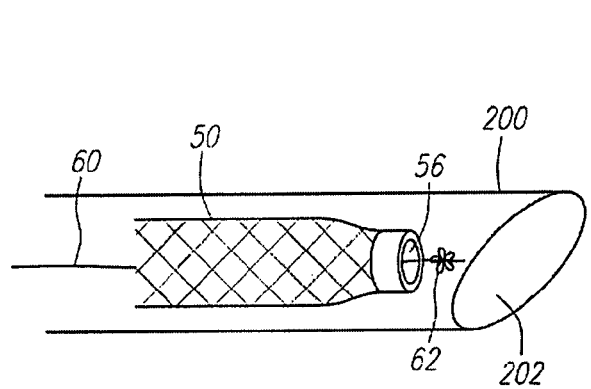
FIG. 11A is a schematic illustration showing an open-ended mesh anchor retained in its delivery configuration within a needle of a delivery device.
Figure 11B:
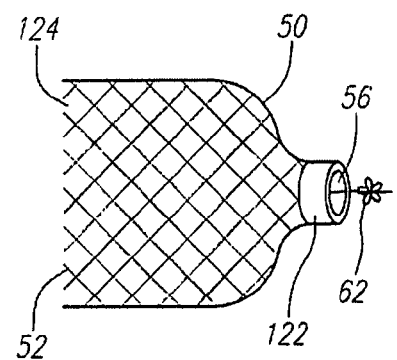
FIG. 11B is a side view of the mesh anchor of FIG. 11A shown after deployment.

FIGS. 11A-B and 12A-B illustrate deployment of two of the types of tissue anchors 50 described herein. Turning first to FIGS. 11A-B, a mesh umbrella-type tissue anchor 50 is shown in a delivery configuration inside a needle 200 of a delivery device. (See FIG. 11A). The needle 200 includes a sharp, beveled tip 202 adapted to penetrate tissue. The mesh tissue anchor 50 is collapsed and compressed to be received within the channel of the needle 200. Upon expulsion from the needle 200, the mesh tissue anchor 50 expands into a deployment configuration in which the open end 124 of the mesh expands radially outward to form a contact surface 52. (See FIG. 11B).

Figure 12A:
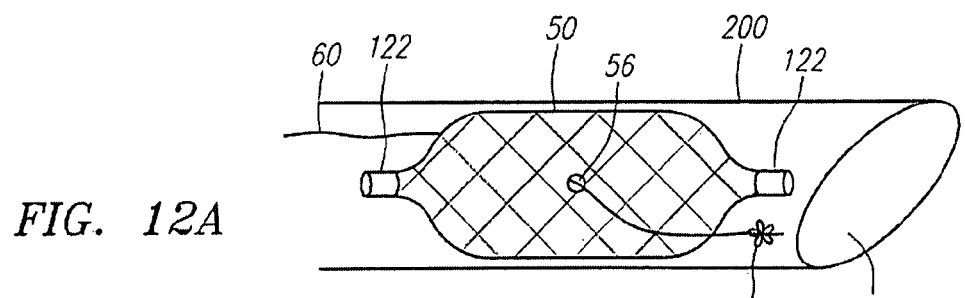
FIG. 12A is a schematic illustration showing an mesh pouch tissue anchor retained in its delivery configuration within a needle of a delivery device.
Figure 12B:
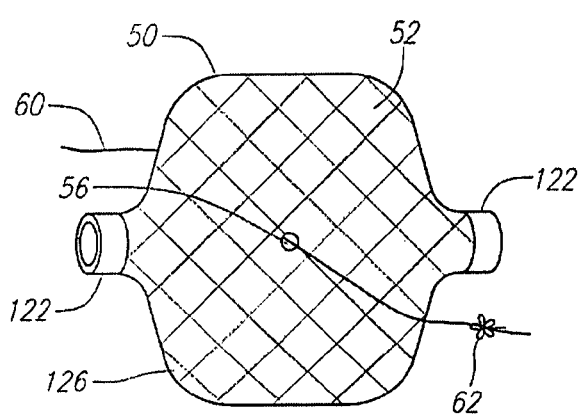
FIG. 12B is a side view of the mesh pouch tissue anchor of FIG. 12A shown after deployment.

In FIGS. 12A-B, a pouch-type mesh anchor 50 is shown in its low-profile delivery configuration (FIG. 12A) and its expanded deployment configuration (FIG. 12B). The pouch 126 is oriented laterally, rather than longitudinally, by the provision of the passage 56 at or near the centroid of the pouch. This orientation provides a large, broad, and flat contact surface 52 for exposure and engagement to the surface of the tissue.

In several embodiments of tissue anchors and tissue anchor assemblies described herein) the tissue anchor includes two or more components that are combined to form a composite tissue anchor. For example, in several embodiments, a mesh pouch or mesh umbrella structure is combined with a "T"-bar or strutted anchor. In those embodiments, the mesh pouch or umbrella is formed over the exterior of the T-bar or strutted anchor, whereby the T-bar or strutted anchor forms a skeletal structure that supports the mesh.

Turning to FIG. 13, a composite tissue anchor 150 includes a mesh umbrella 128 (such as those described above in relation to FIGS. 8B, 9C, and 11B) is laid over or attached to the upper surfaces of a strutted anchor 50 (such as those described above in relation to any of FIGS. 3C-D, 4A-B, 5A-B, and/or 6C). The strutted anchor 50 thereby provides additional support to the mesh umbrella 128. The mesh 128, in turn, provides additional surface contact with the engagement surface of the tissue, and facilitates healing by providing for additional tissue ingrowth.

In FIG. 14, a composite tissue anchor 150 includes a "T"-bar 140 that is retained within the interior of a mesh pouch 126. In the embodiment shown, the T-bar 140 is retained within the pouch 126, but is not attached directly to the pouch, i.e., it is allowed to "float" within the pouch. In other embodiments, the T-bar 140 is attached (e.g., by adhesive, by heat fusing, etc.) to the pouch 126 to be held in a fixed location within the pouch. The T-bar 140 is formed of a rigid material such as titanium, stainless steel, or other suitable metallic or polymeric material. The size and shape of the T-bar 140 is such that the T-bar 140 is able to be retained within the interior of the pouch 126. In the embodiment shown in FIG. 14, the T-bar 140 is substantially rectangular, having a passage 56 formed near its centroid. Other shapes are contemplated in alternative embodiments.

In FIGS. 15A-B, a composite tissue anchor 150 includes a central collar 142 that is applied over or incorporated onto or within a mesh pouch 126. In the embodiment shown, the central collar 142 is located at the approximate midpoint between the two fused ends 122 of the pouch 126, thereby forming a sub-pouch 127 on each side of the collar 142. The central collar 142 is formed of a rigid material and defines a passage 56 therethrough.

In the embodiment shown in FIG. 15B, the composite tissue anchor 150 includes a coil support structure 144 located within each of the sub-pouches 127. Each coil support structure 144 comprises a coil of Nitinol wire or other resilient material that is attached at a first end to a fused end 122 of the pouch and at a second end to the respective side of the central collar 142. The coil support 144 is adapted to be compressed when the composite tissue anchor 150 is in its delivery state, and to expand after the composite tissue anchor 150 has been deployed. A pair of coil supports 144 are included in the embodiment shown in FIG. 15B. In other embodiments, as few as one coil support 144 and as many as three or more coil supports 144 are included in the composite tissue anchor 150.

Turning next to FIG. 16, a composite tissue anchor 150 includes a mesh pouch 126 having a pair of fused ends 122 at opposite ends thereof. A passage 56 is formed at or near the centroid of the pouch 126. A support ring 146 is located within the interior of the mesh pouch 126. In the embodiment shown, the support ring 146 is retained within the pouch 126, but is not attached directly to the pouch, i.e., it is allowed to "float" within the pouch. In other embodiments, the support ring 146 is attached (e.g., by adhesive, by heat fusing, etc.) to the pouch 126 to be held in a fixed location within the pouch. The support ring 146 is formed of a resilient material such as nickel titanium alloy Nitinol), stainless steel, or other suitable metallic or polymeric material. The size and shape of the support ring 146 is such that the support ring 146 is able to be retained within the interior of the pouch 126. In the embodiment shown in FIG. 16, the support ring 146 is substantially circular, and the support ring 146 extends substantially to the outer edges of the pouch 126. Other shapes and sizes for the support ring 146 are contemplated in alternative embodiments.

The support ring 146 is adapted to be collapsed, compressed, or otherwise reduced in profile when the composite tissue anchor 150 is retained within a delivery device or otherwise placed in its delivery state. Upon release from the delivery device, the resilient support ring 146 expands to its deployment state (as shown in FIG. 16), thereby also expanding the pouch 126 into the expanded state. In the embodiment shown, the support ring 146 is a continuous ring of resilient material. The ring is formed by cutting, stamping, or milling a ring shape from a sheet of material. In alternative embodiments, the support ring 146 is formed of a wire or similar member that is formed into a ring shape and attached at its ends, such as by welding, wrapping, or by a suitable collar or other connector.

The support ring 146 provides a degree of shape and support to the composite tissue anchor 150. Accordingly, in some embodiments, a shape or contour is applied to the support ring 146. For example, in an embodiment opposed sides of the support ring 146 are bent out of plane to create a generally concave "C" shape to the composite tissue anchor 150 when viewed in profile. In another embodiment, the support ring 146 is bent into an "S" shape in profile, to provide another variation in the contact surface shape and resiliency. Other shape variations are also contemplated.

Another embodiment of a composite tissue anchor 150 is shown in FIG. 17. The composite anchor 150 includes a frame 148 formed of a resilient material such as nickel-titanium alloy (Nitinol), stainless steel, or other suitable metallic or polymeric material. A mesh sheet 134 or a plurality of mesh sheets is attached to (e.g., by adhesive or heat sealing) and extends across the interior of the frame 148. A passage 56 is formed or located near the centroid of the frame 148. In the embodiment shown in FIG. 17, the frame 148 is generally circular. In other embodiments, the frame 148 has a triangular shape, a square shape, an irregular shape, or another geometric or non-geometric shape.

The frame 148, formed of a resilient material, is adapted to collapse or compress into a low-profile delivery state, such as when the tissue anchor 150 is received within a delivery device (such as a needle 200). Upon expulsion from the delivery device, the frame 148 expands to its deployment state (as shown in FIG. 17).

FIG. 18A shows an exploded view of the components making up another embodiment of a composite tissue anchor 150. FIG. 18B shows the consolidated structure. The composite tissue anchor 150 includes a mesh pouch 126, a support ring 146 retained within the mesh pouch, and a cross-bar 140 also retained within the mesh pouch 126, in the embodiment shown, the support ring 146 is formed of nickel-titanium alloy (Nitinol), stainless steel, or other resilient metallic or polymeric material in the embodiment, the cross-bar 140 is formed of titanium, stainless steel, or other rigid metallic or polymeric material. A passage 56 is defined by the cross-bar 140 and has a size and shape to allow the connector, such as a suture 60, to pass therethrough.

The composite tissue anchor 150 shown in FIGS. 18A-B has a slightly concave shape. The concavity is provided by the shape of the support ring 146 and also by the shape of the mesh pouch 126. In an embodiment, the concavity of the composite tissue anchor 150 enhances the degree of contact that the contact surface 52 has with the engaged tissue.

FIGS. 19A-B illustrate the general operation and some of the features of the tissue anchor assemblies described herein. The distal anchor 50a and suture 60 of the tissue anchor assembly 100 are delivered through a portion of tissue T. Delivery devices and methods of delivery are described in more detail below in relation to FIGS. 21-25. After delivery through the tissue T, the proximal anchor 50b and distal anchor 50a are moved into close proximity to one another to retain the tissue fold F. The cinch 102 is advanced on the suture 60 to bias the proximal anchor 50b toward the proximal anchor 50a. The contact surfaces 52 of the respective anchors 50 engage the surfaces of the tissue fold F.

Although the schematic diagram in FIGS. 19A-B and the associated description refers to tissue anchors 50, the figures and descriptions also apply to the composite tissue anchors 150 and other tissue anchors described herein. In addition, in several embodiments of the tissue anchors 50/150 and tissue anchor assemblies 100 described herein, the tissue anchor 50/150 is subject to being applied against tissue in either its forward orientation (i.e., with the contact surface 52 engaged against the tissue T), or in a reverse orientation (i.e., with the exposed surface 54 engaged against the tissue T). For example, in several of these embodiments, each of the tissue anchors 50/150 described above is deployed in its reverse orientation. In several of these embodiments, the tissue anchor 50/150 in its reverse orientation is capable of performing its tissue anchoring function and is more easily deployed from certain delivery devices due to the shape and resiliency of the main body 51 portion of the anchor.

In addition, for tissue anchor assemblies 100 that incorporate two or more tissue anchors 50/150, several embodiments include tissue anchors of different types within a single tissue anchor assembly. For example, in an embodiment, a tissue anchor assembly 100 includes a first composite tissue anchor 150 such as that described in relation to FIGS. 18A-B above, and a second anchor that comprises a known basket-type anchor. In another embodiment, a tissue anchor assembly 100 includes a first composite tissue anchor 150 such as that described in relation to FIGS. 18A-B above, and a second tissue anchor 50 such as that described above in relation to FIG. 9C. All other combinations of anchor types within a tissue anchor assembly are contemplated, including combinations that include the anchors described herein, combinations that include known tissue anchors, and combinations that include anchors such as those described in U.S. patent application Ser. Nos. 10/612,170; 10/840,950; 10/840,951; 10/841,245; 10/841,411; 10/865,736; 11/036,866; 11/036,946; and 11/404,423, each of which is hereby incorporated by reference in its entirety (including all references cited therein) as if fully set forth herein.

In addition, the tissue anchor assembly shown in FIGS. 19A-B includes a single cinch 102 movably attached to the suture 60 at a point proximal to the proximal anchor 50b. In alternative embodiments, a distal cinch is provided on the suture 60 at a point distal of the distal anchor 50a, in place of (or in addition to) the stop member 62. In this alternative embodiment, the anchors 50a, 50b are able to be brought into proximity to one another and retained via advancement of either the first cinch 102, the distal cinch, or both cinches.

As noted above, a cinch 102 is a suitable member for use as the cinching mechanism included in the tissue anchor assemblies described herein. The cinch 102 functions by providing unidirectional translation over the suture thereby providing the ability to advance the tissue anchor(s) 50/150 into apposition and to retain the anchor(s) in place. An embodiment of a cinch 102 is shown in FIGS. 20A-B. The cinch includes a generally tubular body 103 defining an internal lumen 104. A plurality of inwardly facing levers 105 are formed integrally with the side wall of the tubular body 103. Three levers 103 are included in the cinch embodiment shown in the figures. In other embodiments, fewer levers (e.g., one or two) or more than three levers are used. In some embodiments, each lever 105 is flexibly biased to spring radially inward into the tubular body 103 or to deflect radially outward upon a suture 60 or other connector member passing therethrough. During translation of the suture 60 in a first direction (i.e., from left to right as viewed in FIG. 20B), the suture 60 is allowed to freely pass through the tubular body and past the plurality of levers due to a slight radially outward pivot of each of the levers. However, when the suture is urged in the second direction (i.e., from right to left as viewed in FIG. 20B), the levers 105 pivot radially inward, cinching down upon the suture against the inner surface of the tubular body 103. The cinching levers 105 are configured to prevent or inhibit the overcinching or cutting of the suture 60.

In other embodiments of the cinch 102, the levers 105 are substantially rigid, and do not pivot or deflect. In those embodiments, the levers 105 create a sufficiently tortuous path for the suture 60 (or other connector) to traverse that the cinch effectively binds the suture from translating in the first direction, while allowing translation in the second direction.

The cinches 102 described herein are formed of biocompatible and/or bioabsorbable materials such as those described above. In several embodiments, the cinch is formed of nickel-titanium alloy (Nitinol). The size and shape of the cinch are primarily dependent upon the size and shape of the other parts of the tissue anchor assembly, such as the diameter and materials forming the suture 60 (or other connector) and/or the size of the passage 56 in the tissue anchors 50/150. Additional embodiments of cinches and additional cinching mechanisms suitable for use in the tissue anchor assemblies 100 are described and illustrated in U.S. patent application Ser. Nos. 10/612,170; 10/840,950; 10/840,951; 10/841,245; 10/841,411; 10/865,736; 11/036,866; 11/036,946; and 11/404,423, each of which is hereby incorporated by reference in its entirety (including all references cited therein) as if fully set forth herein.

The tissue anchor assemblies 100 described herein are suitable for use in surgical, diagnostic, and other therapeutic procedures that are performed endoscopically, laparoscopically, endoluminally, or in open procedures. In several embodiments, a suitable delivery device is used to deploy the tissue anchors 50/150 and tissue anchor assemblies 100 endoscopically and/or laparoscopically. An example of a suitable delivery device is shown in FIG. 21, and is described in more detail in U.S. patent application Ser. No. 11/070,846, which is hereby incorporated by reference in its entirety (including all references cited therein) as if fully set forth herein. The delivery device 208 is described briefly below.

In manipulating tissue or creating tissue folds, a device having a distal end effector may be advanced endoluminally, e.g., transorally, transgastrically, etc., into the patient's body, e.g., the stomach. The tissue may be engaged or grasped and the engaged tissue may be manipulated by a surgeon or practitioner from outside the patient's body. Examples of creating and forming tissue plications may be seen in farther detail in U.S. patent application Ser. No. 10/955,245, filed Sep. 29, 2004, which is incorporated herein by reference, as well as U.S. patent application Ser. No. 10/735,030, filed Dec. 12, 2003, which is also incorporated herein by reference in its entirety.

In engaging, manipulating, and/or securing the tissue, various methods and devices may be implemented. For instance, tissue securement devices may be delivered and positioned via an endoscopic apparatus for contacting a tissue wall of the gastrointestinal lumen, creating one or more tissue folds, and deploying one or more tissue anchors through the tissue fold(s). The tissue anchor(s) may be disposed through the muscularis and/or serosa layers of the gastrointestinal lumen.

The delivery device 208 shown in FIG. 21 generally comprises a tissue manipulation assembly 210 and a needle deployment assembly 260. The tissue manipulation assembly 210 includes a flexible catheter or tubular body 212 which is configured to be sufficiently flexible for advancement into a body lumen, e.g., transorally, percutaneously, laparoscopically, etc. The tubular body 212 is configured to be torqueable through various methods, e.g., utilizing a braided tubular construction, such that when a handle 216 is manipulated and/or rotated by a practitioner from outside the patient's body, the longitudinal and/or torquing force is transmitted along the body 212 such that the distal end of the body 212 is advanced, withdrawn, or rotated in a corresponding manner.

A tissue manipulation end effector 214 is located at the distal end of the tubular body 212 and is generally used to contact and form tissue folds and/or to otherwise bring portions of tissue into apposition. The tissue manipulation end effector 214 is connected to the distal end of the tubular body 212 via a pivotable coupling 218. A lower jaw member 220 extends distally from the pivotable coupling 218 and an upper jaw member 222, in this example, is pivotably coupled to the lower jaw member 220 via a jaw pivot 226. The location of the jaw pivot 226 may be positioned at various locations along the lower jaw 220 depending upon a number of factors, e.g., the desired size of the "bite" or opening for accepting tissue between the jaw members, the amount of closing force between the jaw members, etc. One or both jaw members 220, 222 may also have a number of protrusions, projections, grasping teeth, textured surfaces, etc. on the surface or surfaces of the jaw members 220, 222 facing one another to facilitate the adherence of tissue between the jaw members 220, 222.

A launch tube 228 extends from the handle 216, through the tubular body 212, and distally from the end of the tubular body 212 where a distal end of the launch tube 228 is pivotally connected to the upper jaw member 222 at a launch tube pivot 230. A distal portion of the launch tube 228 may be pivoted into position within a channel or groove defined in upper jaw member 222, to facilitate a low-profile configuration of tissue manipulation end effector 214. When articulated, either via the launch tube 228 or other mechanism, the jaw members 220, 222 may be urged into an open configuration to receive tissue in the opening between the jaw members 220, 222.

The launch tube 228 may be advanced from its proximal end at the handle 216 such that the portion of the launch tube 228 that extends distally from the body 212 is forced to rotate at a hinge or pivot 230 and reconfigure itself such that the exposed portion forms a curved or arcuate shape that positions the launch tube opening perpendicularly relative to the upper jaw member 222. The Launch tube 228, or at least the exposed portion of the launch tube 228, may be fabricated from a highly flexible material or it may be fabricated, e.g., from Nitinol tubing material which is adapted to flex, erg., via circumferential slots, to permit bending.

Once the tissue has been engaged between the jaw members 220, 222, a needle deployment assembly 260 is urged through the handle 216, though the tubular body 212, and out through the launch tube 228. The needle deployment assembly 260 may pass through the lower jaw member 220 via a needle assembly opening (not shown in the drawing) defined in the lower jaw member 220 to pierce through the grasped tissue. Once the needle deployment assembly has been passed through the engaged tissue, one or more tissue anchors of a tissue anchor assembly 100 (see FIG. 22) are deployed for securing the tissue, as described in further detail herein and in U.S. patent application Ser. No. 10/955,245, which has been incorporated by reference above.

FIG. 22 shows additional details relating to the needle deployment assembly 260. As mentioned above, a needle deployment assembly 260 may be deployed through the tissue manipulation assembly 210 by introducing needle deployment assembly 260 into the handle 216 and through the tubular body 212, as shown in the assembly view of FIG. 21, such that the needle assembly 266 is advanced from the launch tube and into or through approximated tissue. Once the needle assembly 266 has been advanced through the tissue, the anchor assembly 100 may be deployed or ejected. The anchor assembly 100 is normally positioned within the distal portion of a tubular sheath 264 that extends from a needle assembly control or housing 262. Once the anchor assembly 100 has been fully deployed from the sheath 264, the spent needle deployment assembly 260 may be removed from the tissue manipulation assembly 210 and another needle deployment assembly may be introduced without having to remove the tissue manipulation assembly 210 from the patient. The length of the sheath 264 is such that it may be passed entirely through the length of the tubular body 212 to enable the deployment of the needle assembly 266 into and/or through the tissue.

The elongate and flexible sheath or catheter 264 extends removably from the needle assembly control or housing 262. The sheath or catheter 264 and the housing 262 may be interconnected via an interlock 270 which may be adapted to allow for the securement as well as the rapid release of the sheath 264 from the housing 262 through any number of fastening methods, e.g., threaded connection, press-fit, releasable pin, etc. The needle body 272, which may be configured into any one of the variations described above, extends from the distal end of the sheath 264 while maintaining communication between the lumen of the sheath 264 and the needle opening 274.

An elongate pusher 276 comprises a flexible wire or hypotube that is translationally disposed within the sheath 264 and movably connected within tie housing 262. A proximally-located actuation member 278 is rotatably or otherwise connected to the housing 262 to selectively actuate the translational movement of the elongate pusher 276 relative to the sheath 264 for deploying the anchors from the needle opening 274. The tissue anchor assembly 100 is positioned distally of the elongate pusher 276 within the sheath 264 for deployment from the sheath 264. Needle assembly guides 280 protrude from the housing 262 for guidance through the locking mechanism described above.

Several embodiments of the needle body 272 and the orientation of the needle opening 274 are shown in FIGS. 23A-C. In the embodiment shown in FIG. 23A, the needle body 272 includes an end configuration that incorporates an edge having a single grind or cut point 282. In the embodiment shown in FIG. 23B, the end configuration incorporates a multi-faceted edge 284. In the embodiment shown in FIG. 23C, the end configuration incorporates a deflected point 286, such as a Tuohy needle. These embodiments are exemplary, and are not intended to be limiting. Other needle body variations are also contemplated to obtain desired results.

For example, in FIGS. 24A-B, another embodiment for the needle body 272 includes a tube 290 having a blunt distal end 292 and a side exit port 294 formed through the side wall at a short distance from die distal end 292. An insert 295 is located within the distal portion of the tube 290. The insert 295 includes an inclined surface 296 facing proximally within die tube 290 and aligned with the side exit port 294, and a piercing surface 297 formed on the distal end, extending longitudinally from the distal end of the tube 290. The inclined surface 296 and exit port 294 operate to provide a ramp and exit port for deployment of a tissue anchor or tissue anchor assembly via a side port exit, rather than a straight, distal port exit. Although described and illustrated as separate structures, the tube 290 and insert 295 may also be formed as a single structure.

When a tissue anchor 50/150 is deployed from a delivery device having a needle deployment assembly 260, a side-oriented exit port from the needle body 272 may facilitate a preferred orientation of the anchor 50/150 relative to tie tissue. For example, as shown in FIGS. 25A-C, after expulsion from the needle body 272, a flat tissue anchor 150 must toggle relative to the suture 60 in order to be properly oriented relative to the surface of the tissue T. If the anchor 150 does not toggle, and instead remains generally aligned with the suture 60, the possibility is increased that the anchor 150 will pull through the channel in the tissue T created by the needle body 272 as the needle is retracted after delivery of the anchor 150. In the embodiment shown, the needle body 272 includes an end configuration that includes a deflected point 286. As a result, the needle opening 274 is oriented at an angle α relative to the longitudinal axis A of the needle body 272. Accordingly, as the tissue anchor 150 is deployed, the longitudinal axis of the tissue anchor 150 is effectively "pre-toggled," i.e., shifted from its alignment with the needle tract, thereby reducing the likelihood of pull through. A similar result is obtained using the needle body structure described above in relation to FIGS. 24A-B.

As discussed above, the tissue anchors, tissue anchor assemblies, and delivery devices described herein are suitable for use in a variety of surgical, diagnostic, and/or therapeutic procedures in which one or more portions of tissue are to be approximated, brought into apposition, joined, manipulated, or otherwise reconfigured. The devices and methods are particularly suitable for translumenal procedures (e.g., transoral, gastric, or gastroesophageal procedures; transrectal or colonic procedures; transvaginal procedures; natural orifice translumenal endoscopic surgical or "NOTES" procedures; and others). Several translumenal procedures are described in U.S. patent application Ser. No. 10/841,233, Ser. No. 10/898,683, Ser. No. 11/238,279, Ser. No. 11/102,571, Ser. No. 11/342,288, and Ser. No. 11/270,195, which are hereby incorporated by reference. The medical instruments described herein are suitable for use in combination with, for example, the endoluminal tool deployment systems described in U.S. patent application Ser. No. 10/797,485 and Ser. No. 11/738,297, which are hereby incorporated by reference. In particular, the tool deployment systems described in the '485 application and the '297 application include one or more lumens suitable for facilitating deployment of the medical instruments described herein to perform or assist in performing endoscopic, laparoscopic, or NOTES diagnostic or therapeutic procedures.

Although various illustrative embodiments are described above, it will be evident to one skilled in the art that various changes and modifications are within the scope of the invention. It is intended in tie appended claims to cover all such changes and modifications that fall within the true spirit and scope of the invention.

What is claimed is:

1. A tissue anchor assembly, comprising:
   a first tissue anchor comprising a pouch formed of a woven material, a support bar retained within the pouch, and a support ring retained within the pouch;
   a second tissue anchor;
   a connector extending between and interconnecting the first tissue anchor and the second tissue anchor; and
   a first cinching mechanism movably attached to said connector.

2. The tissue anchor assembly of claim 1, further comprising a second cinching mechanism movably attached to said connector, with the first tissue anchor and the second tissue anchor being movably attached to the connector between the first cinching mechanism and the second cinching mechanism.

3. The tissue anchor assembly of claim 1, wherein said cinching mechanism comprises a cinch having a tubular body and at least one lever extending into a lumen defined by said tubular body.

4. The tissue anchor assembly of claim w with the suture and the pouch comprising a bioabsorbable material.

5. The tissue anchor assembly of claim 1, wherein said second tissue anchor is a basket anchor.

6. The tissue anchor assembly of claim 5, wherein said basket anchor comprises a first collar, a second collar, and a plurality of struts extending between and attached to said first collar and said second collar.

7. The tissue anchor assembly of claim 5, wherein said basket anchor comprises a first collar, a second collar, and a woven material extending between and attached to said first collar and said second collar.

8. The tissue anchor assembly of claim 1, wherein said second tissue anchor comprises a pouch formed of a woven material, a support bar retained within the pouch, and a support ring retained within the mesh pouch.

9. The tissue anchor assembly of claim 1, wherein said first tissue anchor comprises a reduced profile delivery configuration and an expanded profile deployment configuration.

10. The tissue anchor assembly of claim 1, further comprising a needle deployment assembly having a handle, a flexible sheath having a proximal end attached to said handle and a distal end attached to a needle body, and a pusher slidably received within the sheath, wherein said tissue anchor assembly is releasably received within the needle body and said pusher is adapted to discharge said tissue anchor assembly from said needle body.

11. The tissue anchor assembly of claim 1, wherein said pouch is formed of a mesh material.

12. The tissue anchor assembly of claim 1. wherein said pouch is formed of a single, continuous layer of material.

13. The tissue anchor assembly of claim 1, wherein said pouch is formed of a plurality of layers of material.

14. The tissue anchor assembly of claim 1. wherein said pouch comprises a sleeve of mesh material having a first end and a second end. with at least one of said first and second ends being heal fused.

15. The tissue anchor assembly of claim 1. wherein said support ring comprises a nickel-titanium alloy.

16. A tissue anchor assembly, comprising.
 a first tissue anchor comprising a pouch of a woven material, a bar within the pouch, and a resilient support ring within the pouch;
 a second tissue anchor:
 a suture extending through the bar and the pouch and connecting the first tissue anchor to the second tissue anchor, and
 a first cinching mechanism on the suture, 17. The tissue anchor assembly of claim 16 with the bar substantially rectangular. Pg, 18. The tissue anchor assembly of claim 17 with the bar having a central passage, and with the suture extending through the central passage.

19. A tissue anchor assembly, comprising:
 a first tissue anchor comprising a pouch of a woven material, a bar within the pouch, and a resilient support ring within the pouch:
 a second tissue anchor;
 a suture extending through the bar and connecting the first tissue anchor to the second tissue anchor; and
 a first cinching mechanism on the suture.

20. The tissue anchor assembly of claim 19 with the pouch formed of a mesh material and having fused opposite ends.

21. The tissue anchor assembly of claim 19 wherein the support ring is substantially circular and extends substantially to the outer edges of the pouch.

22. The tissue anchor assembly of claim 19 with the support ring comprising a continuous ring of resilient material.

* * * * *